US006271026B1

(12) United States Patent
Stone et al.

(10) Patent No.: US 6,271,026 B1
(45) Date of Patent: Aug. 7, 2001

(54) GLAUCOMA COMPOSITIONS

(75) Inventors: Edwin M. Stone, Iowa City; Val C. Sheffield, Coralville; Wallace L. M. Alward, Iowa City, all of IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 08/822,999

(22) Filed: Mar. 21, 1997

(51) Int. Cl.[7] .............................. C12N 5/00; C12N 5/02; C12N 15/00; C12N 15/63
(52) U.S. Cl. ...................... 435/325; 435/320.1; 435/455; 435/456; 435/69.1; 536/23.1; 536/23.5; 536/24.31
(58) Field of Search .................................. 435/320.1, 325, 435/455, 456, 463, 69.1; 536/23.1, 23.5, 24.31; 800/13, 3, 9, 21, 22, 25

(56) References Cited

U.S. PATENT DOCUMENTS

| 5,606,043 | 2/1997 | Nguyen et al. ........................ 536/23.5 |
| 5,789,169 | * 8/1998 | Nguyen et al. ............................ 435/6 |
| 5,849,879 | * 12/1998 | Nguyen et al. ................... 530/387.9 |
| 5,854,415 | * 12/1998 | Nguyen et al. ....................... 536/23.5 |
| 5,861,497 | * 1/1999 | Nguyen et al. ....................... 536/23.5 |

FOREIGN PATENT DOCUMENTS

| WO 96/14411 | 5/1996 | (WO) .............................. C12Q/1/68 |
| WO 96/33287 | 10/1996 | (WO) .............................. C12Q/1/68 |

OTHER PUBLICATIONS

"CHLC Report" (Newsletter), Cooperative Human Linkage Center, vol. 1, pp. 1–18, May 1993.
"Editorial: Genetic Associations of Glaucoma", *British Journal of Ophthalmology*, vol. 64, pp. 225–226, 1980.
Cotton, P., "Glaucoma Gene Mapped to Chromosome 1", *JAMA*, vol. 269, No. 21, p. 2715, Jun. 2, 1993.
Francois, J., "Genetics and Primary Open–Angle Glaucoma", *Am. J. Ophthalmol.*, vol. 61, pp. 652–665, 1966.
Harris, D., "The Inheritance of Glaucoma: A Pedigree of Familial Glaucoma", *Am. J. Ophthalmol.*, vol. 60, pp. 91–95, 1965.
Johnson, A.T. et al., "Clinical Features and Linkage Analysis of a Family with Autosomal Dominant Juvenile Glaucoma", *Ophthalmology*, vol. 100, No. 4, pp. 524–528, Apr. 1993.
Kolker, A.E., "Glaucoma Famliy Study: Ten–Year Follow–up (Preliminary Report)", *Israel J. Med. Sci.*, vol. 8, No. 8–9, pp. 1357–1361, Aug.–Sep. 1972.
Leighton, D.A., "Survey of the First–degree Relatives of Glaucoma Patients", *Trans. Ophthal. Soc. U.K.* vol.. 96, pp. 28–32, 1976.
Martin, J.P. and E.C. Zorab, "Familial Glaucoma in Nine Generations of a South Hampshire Family", *Brit. J. Ophthal.*, pp. 536–542, 1974.

Miller, S.J.H and G.D. Paterson, "Studies on Glaucoma Relatives", *Brit. J. Ophthalmol.*, vol. 46, pp. 513–522, 1962.
Orita, M. et al., "Detection of Polymorphisms of Human DNA by Gel Electrophoresis as Single–Strand Conformation Polymorphisms", *Proc. Natl. Acad. Sci. USA*, vol. 86, pp. 2766–2770, Apr. 1989.
Perkins, E.S., "Family Studies in Glaucoma", *Brit. J. Ophthal.*, vol. 58, pp. 529–535, 1974.
Richards, J.E. et al., "Mapping of a Gene for Autosomal Dominant Juvenile–Onset Open–Angle Glaucoma to Chromosome Iq", *Am. J. Hum. Genet.*, vol. 54, pp. 62–70, 1994.
Sheffield, V.C., et al., "Attachment of a 40–Base–Pair G+C–Rich Sequence (GC–clamp) to Genomic DNA Fragments by the Polymerase Chain Reaction Results in Improved Detection of Single–Base Changes", *Proc. Natl. Acad. Sci. USA*, vol. 86, pp. 232–236, Jan. 1989.
Sheffield, V.C., et al., "Genetic Linkage of Familial Open Angle Glaucoma to Chromosome 1q21–q31", *Nature Genetics*, vol. 4, pp. 47–50, May 1993.
Weatherill, J.R. and Hart, C.T., "Familial Hypoplasia of the Iris Stroma Associated with Glaucoma" *Brit. J. Ophthal.*, vol. 53, pp. 433–438, 1969; and.
Escribano, J., et al., "Isolation and Characterization of Cell–Specific cDNA Clones from a Subtractive Library of the Ocular Ciliary Body of a Single Normal Human Donor: Transcription and Synthesis of Plasma Proteins", *J. Biochem.*, vol. 118, pp. 921–931, 1995.
Ortega, J. et al., (1997) "Cloning and Characterization of Subtracted cDNAs from a Human Ciliary Body Library Encoding TIGR, a Protein Involved in Juvenile Open Angle Glaucoma with Homology to Myosin and Olfactomedin", *FEBS Letters*, 413:349–353.
Stone, Edwin M. et al. (1997) "Identification of a Gene that Causes Primary Open Angle Glaucoma", *Science*, 275:668–670.
Sunden, Sara L.F. et al. (1996) "Fine Mapping of the Autosomal Dominant Juvenile Open Angle Glaucoma (GLC1A) Region and Evaluation of Candidate Genes" *Genome Res.*, 6:862–869; and.
Database entry HSU85257 GenBank No. U85257, US Library of Medicine, (Bethesda, MD, USA), Mar. 2, 1997 (Stone et al.).
Houdebine, Journal of Biotechnology, vol. 34, pp. 269–287, 1994.*
Hammer et al., Journal of Animal Science, vol. 63, pp. 269–278, 1986.*
Ebert et al., Molecular Endocrinology, vol. 2, pp. 277–283, 1988.*

(List continued on next page.)

*Primary Examiner*—Jill D. Martin
(74) *Attorney, Agent, or Firm*—Foley, Hoag & Eliot LLP; Beth E. Arnold; Anita Varma

(57) ABSTRACT

Glaucoma compositions comprising the GLC1A gene are disclosed.

6 Claims, 6 Drawing Sheets

OTHER PUBLICATIONS

Figure 2:
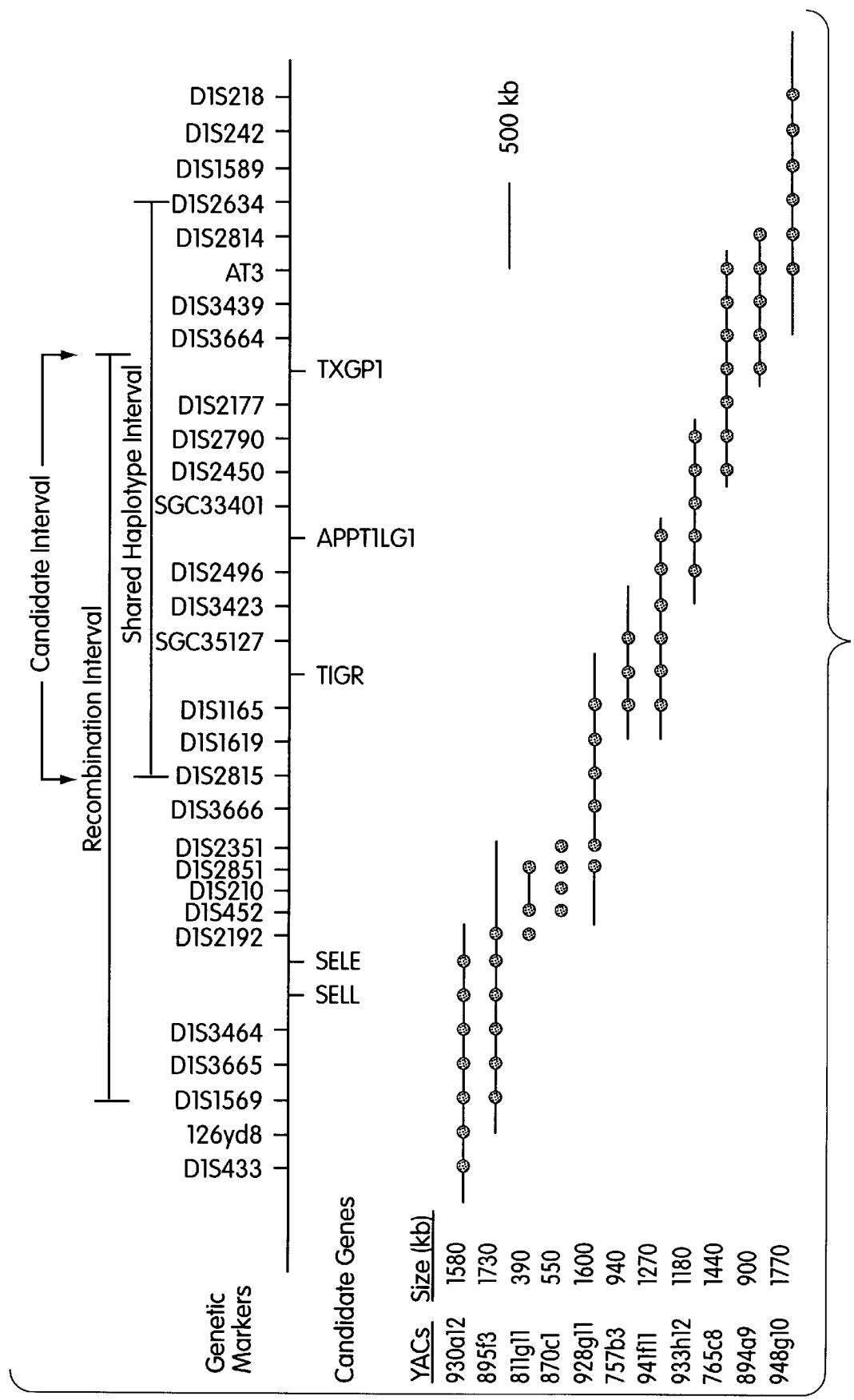

Mullins et al., Journal of Clinical Investigations, vol. 98, pp. S37–S40, 1996.*

Wall, Theriogenology, vol. 45, pp. 57–68, 1996.*

Kappel et al., Current Opinion in Biotechnology, vol. 3, pp. 548–553, 1992.*

Strojek & Wagner, Genetic Engineering, vol. 10, pp. 221–246, 1988.*

Moreadith et al., J. Mol. Med., vol. 75, pp. 208–216, 1997.*

Seamark, Reproductive Fertility and Development, vol. 6, pp. 653–657, 1994.*

Eck & Wilson, 'Gene–Based Therapy' in Goodman & Gilman's The Pharmacological Basis of Therapeutics, McGraw–Hill: New York, Ninth Edition, pp. 77–101, 1995.*

* cited by examiner

GLC1A genomic sequence 3/12/97

3'UTR (TATA box -107 to -98):

```
CCCCCNTGTG CACAGCCCCA CCCAGCCTCA NGTGGCCACT TNTGTCTTCC
CCCATGAAGG GCTGGCTCCC CAGTATATAT AAACNTNTNT GGAGNTCGGG
CATGAGCCAG CAAGGCCACC CATTCAGGCA CCTTTCAGCA CAGCAGAGCT
TTCCAGAGGA AGCCTCACCA AGCCTCTGCA
```

Exon 1:

```
ATGAGGTTCT TCTGTGCACG TTGCTGCAGC TTTGGGCCTG AGATGCCAGC
TGTCCAGCTG CTGCTTCTGG CCTGCCTGGT GTGGGATGTG GGGGCCAGGA
CAGCTCAGCT CAGGAAGGCC AATGACCAGA GTGGCCGATG CCAGTATACC
TTCAGTGTGG CCAGTCCCAA TGAATCCAGC TGCCCAGAGC AGAGCCAGGC
CATGTCAGTC ATCCATAACT TACAGAGAGA CAGCAGCACC CAACGCTTAG
ACCTGGAGGC CACCAAAGCT CGACTCAGCT CCCTGGAGAG CCTCCTCCAC
CAATTGACCT TGGACCAGGC TGCCAGGCCC CAGGAGACCC AGGAGGGGCT
GCAGAGGGAG CTGGGCACCC TGAGGCGGGA GCGGGACCAG CTGGAAACCC
AAACCAGAGA GTTGGAGACT GCCTACAGCA ACCTCCTCCG AGACAAGTCA
GTTCTGGAGG AAGAGAAGAA GCGACTAAGG CAAGAAAATG AGAATCTGGC
CAGGAGGTTG GAAAGCAGCA GCCAGGAGGT ANCAAGGCTG AGAAGGGGCC
AGTGTCCCCA GACCCGAGAC ACTGCTCGGG CTGTGCCACC AGGCTCCAGA
GAAG
```

Intron 1 (5'end):

```
GTAAGAATGC AGAGTGGGGG GACTCTGAGT TCAGCAGGTG ATATGGCTCG
TAGTGACCTG CTACAGGCGC TCCAGGCCTC CCTGCCTGCC CTTTCTCCTA
GAGACTGCAC AGCTAGCACA AGACAGATGA ATTAAGGAAA GCACAGCGAT
CACCTTCAAG TATTACTAGT AATTTAGCTC CTGAGAGCTT CATTTAGATT
AGTGGTTCAG AGTTCTTGTG CCCCTCCATG TCAGTTTTCA CAGTCCATAG
CAAAAGGAGA AATAAAGGA CCGGGTGAGA TGTGTCTGCA TATGAGCAGT
ANAAGTTGT CAATTGTCCC TTTTGAAAAA CTATCCTTTT TTGAACCTTT
GCTCAGATTG TTATTTGTAC CTTTTGATGT TAAAATGACC TTTATTTATG
AAATTACCAT AGATTGGGAA ATGATAATAA GTGGTAAGTT TTGTTTATTT
TTAAATGTTC TTCCCTGGCA AAATAAAGAG ATGGCACCTC TCTGTCAGTT
TTCTTAATAT GTTGTTCTGA AAGTTTTCTT ACTCAGTCCA ATCTGAGAAC
CTCTGCTTTT AAGTCATCAG ACAAATTCTT GAGATGGCTT TTTCTGANAN
GCTCTTCTGT TCATCCTGGT CCCTTCTTGC CTAAAGGTAA TT....
```

Exon 2:

```
TTTCTACGTG GAATTTGGAC ACTTTGGCCT TCCAGGAACT GAAGTCCGAG
CTAACTGAAG TTCCTGCTTC CCGAATTTTG AAGGAGAGCC CATCTGGCTA
TCTCAGGAGT GGAGAGGGAG ACACCG
```

Fig. 1A

Intron 2 (5' end):

```
GTATGAAGTT AAGTTTCTTC CCTTTTGTGC CCACATGGTC TTTATTCATG
TCTAGTGCTG TGTTCAGAGA ATCAGTATAG GGTAAATGCC CACCCAAGGG
GGAAATTAAC TTCCCTGGGA GCAGAGGGAG GGGAGGAGAA GAGGAACAGA
ACTCTCTCTC TCTCTCTGTT CCCTTGTCAG AGCAGGTCTG CAGGAGTCAG
CCTTTCCCTA ACAAAGCCCT CTATCCTATC ACCCACACTT GGGAGGCTGG
GCTGGGCTGC ACAGGGCAAG ATGAGAGATG TGTTGATTTC ATCCACTTGA
TTGTCATGTA GAATTAGATA TACTTGAGAA GTTACATTTT TCAGTAGCGC
CTTCATATC
```

Intron 2 (3' end):

```
ACAGATTGAT CATATAGCAT TTACCATATA TTTACTCTAT ACCAAGCACT
TAACATATAT AATTACATTT AAAATTTACA ACAGCCCTAC TACCCAAAAC
ACTATTAGTA TCCCCTTTTA CACATGCGAT AACTGAGGCG TAGAGAGCTA
AGTAACTTAC TGAAAGTCAC ACAGCCAGCG GGTGGTAGAG CCTAGCTTTA
AACCCAGACG ATTTGTCTCC AGGGCTGTCA CATCTACTGC TCTGCCAAGC
TTCCGCATGA TCATTGTCTG TGTTTGGAAA GATTATGGAT TAAGTGGTGC
TTCGTTTTCT TTTCTGAATT TACCAG
```

Exon 3:

```
GATGTGGAGA ACTAGTTTGG GTAGGAGAGC CTCTCACGCT GAGAACAGCA
GAAACAATTA CTGGCAAGTA TGGTGTGTGG ATGCGAGACC CCAAGCCCAC
CTACCCCTAC ACCCAGGAGA CCACGTGGAG AATCGACACA GTTGGCACGG
ATGTCCGCCA GGTTTTGAG TATGACCTCA TCAGCCAGTT TATGCAGGGC
TACCCTTCTA AGGTTCACAT ACTGCCTAGG CCACTGGAAA GCACGGGTGC
TGTGGTGTAC TCGGGAGCC TCTATTTCCA GGGCGCTGAG TCCAGAACTG
TCATAAGATA TGAGCTGAAT ACCGAGACAG TGAAGGCTGA GAAGGAAATC
CCTGGAGCTG GCTACCACGG ACAGTTCCCG TATTCTTGGG GTGGCTACAC
GGACATTGAC TTGGCTGTGG ATGAAGCAGG CCTCTGGGTC ATTTACAGCA
CCGATGAGGC CAAAGGTGCC ATTGTCCTCT CCAAACTGAA CCCAGAGAAT
CTGGAACTCG AACAAACCTG GGAGACAAAC ATCCGTAAGC AGTCAGTCGC
CAATGCCTTC ATCATCTGTG GCACCTTGTA CACCGTCAGC AGCTACACCT
CAGCAGATGC TACCGTCAAC TTTGCTTATG ACACAGGCAC AGGTATCAGC
AAGACCCTGA CCATCCCATT CAAGAACCGC TATAAGTACA GCAGCATGAT
TGACTACAAC CCCCTGGAGA AGAAGCTCTT TGCCTGGGAC AACTTGAACA
TGGTCACTTA TGACATCAAG CTCTCCAAGA TG
```

3' UTR:

```
TGAAAAGCCT CCAAGCTGTA CAGGCAATGG CAGAAGGAGA TGCTCAGGGC
TCCTGGGGGG AGCAGGCTGA AGGGAGAGCC AGCCAGCCAG GCCCAGGCA
GCTTTGACTG CTTTCCAAGT TTTCATTAAT CCAGAAGGAT GAACATGGTC
ACCATCTAAC TATTCAGGAA TTGTAGTCTG AGGGCGTAGA CAATTTCATA
TAATAAATAT CCTTTATCTT CTGTCAGCAT TTATGGGATG TTTAATGACA
TAGTTCAAGT TTTCTTGTGA TTTGGGGCAA AAGCTGTAAG GCATAATAGT
TTCTTCCTGA AAACCATTGC TCTTGCATGT TACATGGTTA CCACAAGCCA
CAATAAAAAG CATAACTTCT AAAGGAAGCA GAATANCTCC TCTGGCCAGC
ATCGAATATA AGTAAGATGC ATTTACTACA GTTGGCTTCT AATGCTTCAN
ATAAAATACA GTTGGGTCTC ACAT
```

Fig. 1B

405
GAA CTC GAA CAA ACC TGG GAG ACA AAC ATC

415
CGT AAG CAG TCA GTC GCC AAT GCC TTC ATC

425
ATC TGT GGC ACC TTG TAC ACC GTC AGC AGC
                                CAC(TYR430HIS)
435
TAC ACC TCA GCA GAT GCT ACC GTC AAC TTT

445
GCT TAT GAC ACA GGC ACA GGT ATC AGC AAG

455
ACC CTG ACC ATC CCA TTA AAG AAC CGC TAT

465
AAG TAC AGC AGC ATG

Fig. 3A

310
ATA CTG CCT AGG CCA CTG GAA AGC ACG GGT

320
GCT GTG GTG TAC TCG GGG AGC CTC TAT TTC

330
CAG GGC GCT GAG TCC AGA ACT GTC ATA AGA

340
TAT GAG CTG AAT ACC GAG ACA GTG AAG GCT
TAC(TYR340TYR)
350
GAG AAG GAA ATC CCT GGA GCT GGC TAC CAC
                                GTC(GLY357VAL)
360
GGA CAG TTC CCG TAT TCT TGG GGT GGC TAC
       TAG(GLN361STOP)
370
 ACG GAC ATT G

Fig. 3B

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 2166 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CCCCCNTGTG CACAGCCCCA CCCAGCCTCA NGTGGCCACT TNTGTCTTCC CCCATGAAGG      60

GCTGGCTCCC CAGTATATAT AAACNTNTNT GGAGNTCGGG CATGAGCCAG CAAGGCCACC     120

CATTCAGGCA CCTTTCAGCA CAGCAGAGCT TTCCAGAGGA AGCCTCACCA AGCCTCTGCA     180

ATGAGGTTCT TCTGTGCACG TTGCTGCAGC TTTGGGCCTG AGATGCCAGC TGTCCAGCTG     240

CTGCTTCTGG CCTGCCTGGT GTGGGATGTG GGGGCCAGGA CAGCTCAGCT CAGGAAGGCC     300
```

```
AATGACCAGA GTGGCCGATG CCAGTATACC TTCAGTGTGG CCAGTCCCAA TGAATCCAGC        360

TGCCCAGAGC AGAGCCAGGC CATGTCAGTC ATCCATAACT TACAGAGAGA CAGCAGCACC        420

CAACGCTTAG ACCTGGAGGC CACCAAAGCT CGACTCAGCT CCCTGGAGAG CCTCCTCCAC        480

CAATTGACCT TGGACCAGGC TGCCAGGCCC CAGGAGACCC AGGAGGGGCT GCAGAGGGAG        540

CTGGGCACCC TGAGGCGGGA GCGGGACCAG CTGGAAACCC AAACCAGAGA GTTGGAGACT        600

GCCTACAGCA ACCTCCTCCG AGACAAGTCA GTTCTGGAGG AAGAGAAGAA GCGACTAAGG        660

CAAGAAAATG AGAATCTGGC CAGGAGGTTG GAAAGCAGCA GCCAGGAGGT ANCAAGGCTG        720

AGAAGGGGCC AGTGTCCCCA GACCCGAGAC ACTGCTCGGG CTGTGCCACC AGGCTCCAGA        780

GAAGTTTCTA CGTGGAATTT GGACACTTTG GCCTTCCAGG AACTGAAGTC CGAGCTAACT        840

GAAGTTCCTG CTTCCCGAAT TTTGAAGGAG AGCCCATCTG GCTATCTCAG GAGTGGAGAG        900

GGAGACACCG GATGTGGAGA ACTAGTTTGG GTAGGAGAGC CTCTCACGCT GAGAACAGCA        960

GAAACAATTA CTGGCAAGTA TGGTGTGTGG ATGCGAGACC CCAAGCCCAC CTACCCCTAC       1020

ACCCAGGAGA CCACGTGGAG AATCGACACA GTTGGCACGG ATGTCCGCCA GGTTTTTGAG       1080

TATGACCTCA TCAGCCAGTT TATGCAGGGC TACCCTTCTA AGGTTCACAT ACTGCCTAGG       1140

CCACTGGAAA GCACGGGTGC TGTGGTGTAC TCGGGGAGCC TCTATTTCCA GGGCGCTGAG       1200

TCCAGAACTG TCATAAGATA TGAGCTGAAT ACCGAGACAG TGAAGGCTGA GAAGGAAATC       1260

CCTGGAGCTG GCTACCACGG ACAGTTCCCG TATTCTTGGG GTGGCTACAC GGACATTGAC       1320

TTGGCTGTGG ATGAAGCAGG CCTCTGGGTC ATTTACAGCA CCGATGAGGC CAAAGGTGCC       1380

ATTGTCCTCT CCAAACTGAA CCCAGAGAAT CTGGAACTCG AACAAACCTG GGAGACAAAC       1440

ATCCGTAAGC AGTCAGTCGC CAATGCCTTC ATCATCTGTG GCACCTTGTA CACCGTCAGC       1500

AGCTACACCT CAGCAGATGC TACCGTCAAC TTTGCTTATG ACACAGGCAC AGGTATCAGC       1560

AAGACCCTGA CCATCCCATT CAAGAACCGC TATAAGTACA GCAGCATGAT TGACTACAAC       1620

CCCCTGGAGA GAAGCTCTT TGCCTGGGAC AACTTGAACA TGGTCACTTA TGACATCAAG       1680

CTCTCCAAGA TGTGAAAAGC CTCCAAGCTG TACAGGCAAT GGCAGAAGGA GATGCTCAGG       1740

GCTCCTGGGG GGAGCAGGCT GAAGGGAGAG CCAGCCAGCC AGGGCCCAGG CAGCTTTGAC       1800

TGCTTTCCAA GTTTTCATTA ATCCAGAAGG ATGAACATGG TCACCATCTA ACTATTCAGG       1860

AATTGTAGTC TGAGGGCGTA GACAATTTCA TATAATAAAT ATCCTTTATC TTCTGTCAGC       1920

ATTTATGGGA TGTTTAATGA CATAGTTCAA GTTTTCTTGT GATTTGGGGC AAAAGCTGTA       1980

AGGCATAATA GTTTCTTCCT GAAAACCATT GCTCTTGCAT GTTACATGGT TACCACAAGC       2040

CACAATAAAA AGCATAACTT CTAAAGGAAG CAGAATANCT CCTCTGGCCA GCATCGAATA       2100

TAAGTAAGAT GCATTTACTA CAGTTGGCTT CTAATGCTTC ANATAAAATA CAGTTGGGTC       2160

TCACAT                                                                  2166
```

(2) INFORMATION FOR SEQ ID NO:2:

(i) SEQUENCE CHARACTERISTICS:
    (A) LENGTH: 1512 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1512

(xi) SEQUENCE DESCRIPTION: SEQ ID NO:2:

```
ATG AGG TTC TTC TGT GCA CGT TGC TGC AGC TTT GGG CCT GAG ATG CCA      48
Met Arg Phe Phe Cys Ala Arg Cys Cys Ser Phe Gly Pro Glu Met Pro
1               5                   10                  15

GCT GTC CAG CTG CTG CTT CTG GCC TGC CTG GTG TGG GAT GTG GGG GCC      96
Ala Val Gln Leu Leu Leu Leu Ala Cys Leu Val Trp Asp Val Gly Ala
            20                  25                  30

AGG ACA GCT CAG CTC AGG AAG GCC AAT GAC CAG AGT GGC CGA TGC CAG     144
Arg Thr Ala Gln Leu Arg Lys Ala Asn Asp Gln Ser Gly Arg Cys Gln
        35                  40                  45

TAT ACC TTC AGT GTG GCC AGT CCC AAT GAA TCC AGC TGC CCA GAG CAG     192
Tyr Thr Phe Ser Val Ala Ser Pro Asn Glu Ser Ser Cys Pro Glu Gln
    50                  55                  60

AGC CAG GCC ATG TCA GTC ATC CAT AAC TTA CAG AGA GAC AGC AGC ACC     240
Ser Gln Ala Met Ser Val Ile His Asn Leu Gln Arg Asp Ser Ser Thr
65                  70                  75                  80

CAA CGC TTA GAC CTG GAG GCC ACC AAA GCT CGA CTC AGC TCC CTG GAG     288
Gln Arg Leu Asp Leu Glu Ala Thr Lys Ala Arg Leu Ser Ser Leu Glu
                85                  90                  95

AGC CTC CTC CAC CAA TTG ACC TTG GAC CAG GCT GCC AGG CCC CAG GAG     336
Ser Leu Leu His Gln Leu Thr Leu Asp Gln Ala Ala Arg Pro Gln Glu
            100                 105                 110

ACC CAG GAG GGG CTG CAG AGG GAG CTG GGC ACC CTG AGG CGG GAG CGG     384
Thr Gln Glu Gly Leu Gln Arg Glu Leu Gly Thr Leu Arg Arg Glu Arg
        115                 120                 125

GAC CAG CTG GAA ACC CAA ACC AGA GAG TTG GAG ACT GCC TAC AGC AAC     432
Asp Gln Leu Glu Thr Gln Thr Arg Glu Leu Glu Thr Ala Tyr Ser Asn
    130                 135                 140

CTC CTC CGA GAC AAG TCA GTT CTG GAG GAA GAG AAG AAG CGA CTA AGG     480
Leu Leu Arg Asp Lys Ser Val Leu Glu Glu Glu Lys Lys Arg Leu Arg
145                 150                 155                 160

CAA GAA AAT GAG AAT CTG GCC AGG AGG TTG GAA AGC AGC AGC CAG GAG     528
Gln Glu Asn Glu Asn Leu Ala Arg Arg Leu Glu Ser Ser Ser Gln Glu
                165                 170                 175

GTA NCA AGG CTG AGA AGG GGC CAG TGT CCC CAG ACC CGA GAC ACT GCT     576
Val Xaa Arg Leu Arg Arg Gly Gln Cys Pro Gln Thr Arg Asp Thr Ala
            180                 185                 190

CGG GCT GTG CCA CCA GGC TCC AGA GAA GTT TCT ACG TGG AAT TTG GAC     624
Arg Ala Val Pro Pro Gly Ser Arg Glu Val Ser Thr Trp Asn Leu Asp
        195                 200                 205

ACT TTG GCC TTC AGG AA CTG AAG TCC GAG CTA ACT GAA GTT CCT GCT     672
Thr Leu Ala Phe Gln Glu Leu Lys Ser Glu Leu Thr Glu Val Pro Ala
    210                 215                 220

TCC CGA ATT TTG AAG GAG AGC CCA TCT GGC TAT CTC AGG AGT GGA GAG     720
Ser Arg Ile Leu Lys Glu Ser Pro Ser Gly Tyr Leu Arg Ser Gly Glu
225                 230                 235                 240

GGA GAC ACC GGA TGT GGA GAA CTA GTT TGG GTA GGA GAG CCT CTC ACG     768
Gly Asp Thr Gly Cys Gly Glu Leu Val Trp Val Gly Glu Pro Leu Thr
                245                 250                 255

CTG AGA ACA GCA GAA ACA ATT ACT GGC AAG TAT GGT GTG TGG ATG CGA     816
Leu Arg Thr Ala Glu Thr Ile Thr Gly Lys Tyr Gly Val Trp Met Arg
            260                 265                 270

GAC CCC AAG CCC ACC TAC CCC TAC ACC CAG GAG ACC ACG TGG AGA ATC     864
Asp Pro Lys Pro Thr Tyr Pro Tyr Thr Gln Glu Thr Thr Trp Arg Ile
        275                 280                 285

GAC ACA GTT GGC ACG GAT GTC CGC CAG GTT TTT GAG TAT GAC CTC ATC     912
Asp Thr Val Gly Thr Asp Val Arg Gln Val Phe Glu Tyr Asp Leu Ile
    290                 295                 300
```

```
AGC CAG TTT ATG CAG GGC TAC CCT TCT AAG GTT CAC ATA CTG CCT AGG      960
Ser Gln Phe Met Gln Gly Tyr Pro Ser Lys Val His Ile Leu Pro Arg
305                 310                 315                 320

CCA CTG GAA AGC ACG GGT GCT GTG GTG TAC TCG GGG AGC CTC TAT TTC     1008
Pro Leu Glu Ser Thr Gly Ala Val Val Tyr Ser Gly Ser Leu Tyr Phe
                325                 330                 335

CAG GGC GCT GAG TCC AGA ACT GTC ATA AGA TAT GAG CTG AAT ACC GAG     1056
Gln Gly Ala Glu Ser Arg Thr Val Ile Arg Tyr Glu Leu Asn Thr Glu
            340                 345                 350

ACA GTG AAG GCT GAG AAG GAA ATC CCT GGA GCT GGC TAC CAC GGA CAG     1104
Thr Val Lys Ala Glu Lys Glu Ile Pro Gly Ala Gly Tyr His Gly Gln
        355                 360                 365

TTC CCG TAT TCT TGG GGT GGC TAC ACG GAC ATT GAC TTG GCT GTG GAT     1152
Phe Pro Tyr Ser Trp Gly Gly Tyr Thr Asp Ile Asp Leu Ala Val Asp
370                 375                 380

GAA GCA GGC CTC TGG GTC ATT TAC AGC ACC GAT GAG GCC AAA GGT GCC     1200
Glu Ala Gly Leu Trp Val Ile Tyr Ser Thr Asp Glu Ala Lys Gly Ala
385                 390                 395                 400

ATT GTC CTC TCC AAA CTG AAC CCA GAG AAT CTG GAA CTC GAA CAA ACC     1248
Ile Val Leu Ser Lys Leu Asn Pro Glu Asn Leu Glu Leu Glu Gln Thr
                405                 410                 415

TGG GAG ACA AAC ATC CGT AAG CAG TCA GTC GCC AAT GCC TTC ATC ATC     1296
Trp Glu Thr Asn Ile Arg Lys Gln Ser Val Ala Asn Ala Phe Ile Ile
            420                 425                 430

TGT GGC ACC TTG TAC ACC GTC AGC AGC TAC ACC TCA GCA GAT GCT ACC     1344
Cys Gly Thr Leu Tyr Thr Val Ser Ser Tyr Thr Ser Ala Asp Ala Thr
        435                 440                 445

GTC AAC TTT GCT TAT GAC ACA GGC ACA GGT ATC AGC AAG ACC CTG ACC     1392
Val Asn Phe Ala Tyr Asp Thr Gly Thr Gly Ile Ser Lys Thr Leu Thr
450                 455                 460

ATC CCA TTC AAG AAC CGC TAT AAG TAC AGC AGC ATG ATT GAC TAC AAC     1440
Ile Pro Phe Lys Asn Arg Tyr Lys Tyr Ser Ser Met Ile Asp Tyr Asn
465                 470                 475                 480

CCC CTG GAG AAG AAG CTC TTT GCC TGG GAC AAC TTG AAC ATG GTC ACT     1488
Pro Leu Glu Lys Lys Leu Phe Ala Trp Asp Asn Leu Asn Met Val Thr
                485                 490                 495

TAT GAC ATC AAG CTC TCC AAG ATG                                     1512
Tyr Asp Ile Lys Leu Ser Lys Met
                500
```

(2) INFORMATION FOR SEQ ID NO:3:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO:3:

```
Met Arg Phe Phe Cys Ala Arg Cys Cys Ser Phe Gly Pro Glu Met Pro
1               5                   10                  15

Ala Val Gln Leu Leu Leu Leu Ala Cys Leu Val Trp Asp Val Gly Ala
            20                  25                  30

Arg Thr Ala Gln Leu Arg Lys Ala Asn Asp Gln Ser Gly Arg Cys Gln
        35                  40                  45

Tyr Thr Phe Ser Val Ala Ser Pro Asn Glu Ser Ser Cys Pro Glu Gln
    50                  55                  60

Ser Gln Ala Met Ser Val Ile His Asn Leu Gln Arg Asp Ser Ser Thr
65              70                  75                  80
```

```
Gln Arg Leu Asp Leu Glu Ala Thr Lys Ala Arg Leu Ser Ser Leu Glu
                85                  90                  95

Ser Leu Leu His Gln Leu Thr Leu Asp Gln Ala Ala Arg Pro Gln Glu
            100                 105                 110

Thr Gln Glu Gly Leu Gln Arg Glu Leu Gly Thr Leu Arg Arg Glu Arg
        115                 120                 125

Asp Gln Leu Glu Thr Gln Thr Arg Glu Leu Glu Thr Ala Tyr Ser Asn
    130                 135                 140

Leu Leu Arg Asp Lys Ser Val Leu Glu Glu Lys Lys Arg Leu Arg
145                 150                 155                 160

Gln Glu Asn Glu Asn Leu Ala Arg Arg Leu Glu Ser Ser Gln Glu
            165                 170                 175

Val Xaa Arg Leu Arg Arg Gly Gln Cys Pro Gln Thr Arg Asp Thr Ala
        180                 185                 190

Arg Ala Val Pro Pro Gly Ser Arg Glu Val Ser Thr Trp Asn Leu Asp
        195                 200                 205

Thr Leu Ala Phe Gln Glu Leu Lys Ser Glu Leu Thr Glu Val Pro Ala
    210                 215                 220

Ser Arg Ile Leu Lys Glu Ser Pro Ser Gly Tyr Leu Arg Ser Gly Glu
225                 230                 235                 240

Gly Asp Thr Gly Cys Gly Glu Leu Val Trp Val Gly Glu Pro Leu Thr
                245                 250                 255

Leu Arg Thr Ala Glu Thr Ile Thr Gly Lys Tyr Gly Val Trp Met Arg
            260                 265                 270

Asp Pro Lys Pro Thr Tyr Pro Tyr Thr Gln Glu Thr Thr Trp Arg Ile
        275                 280                 285

Asp Thr Val Gly Thr Asp Val Arg Gln Val Phe Glu Tyr Asp Leu Ile
    290                 295                 300

Ser Gln Phe Met Gln Gly Tyr Pro Ser Lys Val His Ile Leu Pro Arg
305                 310                 315                 320

Pro Leu Glu Ser Thr Gly Ala Val Val Tyr Ser Gly Ser Leu Tyr Phe
                325                 330                 335

Gln Gly Ala Glu Ser Arg Thr Val Ile Arg Tyr Glu Leu Asn Thr Glu
            340                 345                 350

Thr Val Lys Ala Glu Lys Glu Ile Pro Gly Ala Gly Tyr His Gly Gln
        355                 360                 365

Phe Pro Tyr Ser Trp Gly Gly Tyr Thr Asp Ile Asp Leu Ala Val Asp
    370                 375                 380

Glu Ala Gly Leu Trp Val Ile Tyr Ser Thr Asp Glu Ala Lys Gly Ala
385                 390                 395                 400

Ile Val Leu Ser Lys Leu Asn Pro Glu Asn Leu Glu Leu Glu Gln Thr
                405                 410                 415

Trp Glu Thr Asn Ile Arg Lys Gln Ser Val Ala Asn Ala Phe Ile Ile
            420                 425                 430

Cys Gly Thr Leu Tyr Thr Val Ser Ser Tyr Thr Ser Ala Asp Ala Thr
        435                 440                 445

Val Asn Phe Ala Tyr Asp Thr Gly Thr Gly Ile Ser Lys Thr Leu Thr
    450                 455                 460

Ile Pro Phe Lys Asn Arg Tyr Lys Tyr Ser Ser Met Ile Asp Tyr Asn
465                 470                 475                 480

Pro Leu Glu Lys Lys Leu Phe Ala Trp Asp Asn Leu Asn Met Val Thr
                485                 490                 495

Tyr Asp Ile Lys Leu Ser Lys Met
```

500

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

ATACTGCCTA GGCCACTGGA                                                              20

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

CAATGTCCGT GTAGCCACC                                                              19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

GAACTCGAAC AAACCTGGGA                                                             20

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

CATGCTGCTG TACTTATAGC GG                                                         22

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
AGGGGCTGCA GAGGGAGCTG GGCACCCTG                                              29

(2) INFORMATION FOR SEQ ID NO:9:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTAAGAATGC AGAGTGGGGG GACTCTGAGT TCAGCAGGTG ATATGGCTCG TAGTGACCTG      60

CTACAGGCGC TCCAGGCCTC CCTGCCTGCC CTTTCTCCTA GAGACTGCAC AGCTAGCACA     120

AGACAGATGA ATTAAGGAAA GCACAGCGAT CACCTTCAAG TATTACTAGT AATTTAGCTC     180

CTGAGAGCTT CATTTAGATT AGTGGTTCAG AGTTCTTGTG CCCCTCCATG TCAGTTTTCA     240

CAGTCCATAG CAAAAGGAGA AATAAAAGGA CCGGGTGAGA TGTGTCTGCA TATGAGCAGT     300

ANAAAGTTGT CAATTGTCCC TTTTGAAAAA CTATCCTTTT TTGAACCTTT GCTCAGATTG     360

TTATTTGTAC CTTTTGATGT TAAAATGACC TTTATTTATG AAATTACCAT AGATTGGGAA     420

ATGATAATAA GTGGTAAGTT TTGTTTATTT TTAAATGTTC TTCCCTGGCA AAATAAAGAG     480

ATGGCACCTC TCTGTCAGTT TTCTTAATAT GTTGTTCTGA AAGTTTTCTT ACTCAGTCCA     540

ATCTGAGAAC CTCTGCTTTT AAGTCATCAG ACAAATTCTT GAGATGGCTT TTTCTGANAN     600

GCTCTTCTGT TCATCCTGGT CCCTTCTTGC CTAAAGGTAA TT                         642

(2) INFORMATION FOR SEQ ID NO:10:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTATGAAGTT AAGTTTCTTC CCTTTTGTGC CCACATGGTC TTTATTCATG TCTAGTGCTG      60

TGTTCAGAGA ATCAGTATAG GGTAAATGCC CACCCAAGGG GGAAATTAAC TTCCCTGGGA     120

GCAGAGGGAG GGGAGGAGAA GAGGAACAGA ACTCTCTCTC TCTCTCTGTT CCCTTGTCAG     180

AGCAGGTCTG CAGGAGTCAG CCTTTCCCTA ACAAAGCCCT CTATCCTATC ACCCACACTT     240

GGGAGGCTGG GCTGGGCTGC ACAGGGCAAG ATGAGAGATG TGTTGATTTC ATCCACTTGA     300

TTGTCATGTA GAATTAGATA TACTTGAGAA GTTACATTTT TCAGTAGCGC CTTCATATCA     360

CAGATTGATC ATATAGCATT TACCATATAT TTACTCTATA CCAAGCACTT AACATATATA     420

ATTACATTTA AAATTTACAA CAGCCCTACT ACCCAAAACA CTATTAGTAT CCCCTTTTAC     480

ACATGCGATA ACTGAGGCGT AGAGAGCTAA GTAACTTACT GAAAGTCACA CAGCCAGCGG     540

GTGGTAGAGC CTAGCTTTAA ACCCAGACGA TTTGTCTCCA GGGCTGTCAC ATCTACTGCT     600

CTGCCAAGCT TCCGCATGAT CATTGTCTGT GTTTGGAAAG ATTATGGATT AAGTGGTGCT     660

TCGTTTTCTT TTCTGAATTT ACCAG                                           685

(2) INFORMATION FOR SEQ ID NO:11:

(i) SEQUENCE CHARACTERISTICS:
        (A) LENGTH: 195 base pairs
```

(B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GAACTCGAAC AAACCTGGGA GACAAACATC CGTAAGCAGT CAGTCGCCAA TGCCTTCATC      60

ATCTGTGGCA CCTTGTACAC CGTCAGCAGC TACACCTCAG CAGATGCTAC CGTCAACTTT     120

GCTTATGACA CAGGCACAGG TATCAGCAAG ACCCTGACCA TCCCATTCAA GAACCGCTAT     180

AAGTACAGCA GCATG                                                     195

(2) INFORMATION FOR SEQ ID NO:12:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GAACTCGAAC AAACCTGGGA GACAAACATC CGTAAGCAGT CAGTCGCCAA TGCCTTCATC      60

ATCTGTGGCA CCTTGCACAC CGTCAGCAGC TACACCTCAG CAGATGCTAC CGTCAACTTT     120

GCTTATGACA CAGGCACAGG TATCAGCAAG ACCCTGACCA TCCCATTCAA GAACCGCTAT     180

AAGTACAGCA GCATG                                                     195

(2) INFORMATION FOR SEQ ID NO:13:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (xi) SEQUENCE DESCRIPTION: SEQ ID NO:13:

ATACTGCCTA GGCCACTGGA AAGCACGGGT GCTGTGGTGT ACTCGGGGAG CCTCTATTTC      60

CAGGGCGCTG AGTCCAGAAC TGTCATAAGA TATGAGCTGA ATACCGAGAC AGTGAAGGCT     120

GAGAAGGAAA TCCCTGGAGC TGGCTACCAC GGACAGTTCC CGTATTCTTG GGGTGGCTAC     180

ACGGACATTG                                                           190

(2) INFORMATION FOR SEQ ID NO:14:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ATACTGCCTA GGCCACTGGA AAGCACGGGT GCTGTGGTGT ACTCGGGGAG CCTCTATTTC      60

CAGGGCGCTG AGTCCAGAAC TGTCATAAGA TACGAGCTGA ATACCGAGAC AGTGAAGGCT     120

GAGAAGGAAA TCCCTGGAGC TGTCTACCAC GGATAGTTCC CGTATTCTTG GGGTGGCTAC     180

ACGGACATTG                                                           190

(2) INFORMATION FOR SEQ ID NO:15:

```
    (i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ACGGACAGTT C                                                            11

(2) INFORMATION FOR SEQ ID NO:16:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ACGGATAGTT C                                                            11

(2) INFORMATION FOR SEQ ID NO:17:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GAACTGTCCG T                                                            11

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GAACTATCCG T                                                            11
```

GLAUCOMA COMPOSITIONS

1. GOVERNMENT SUPPORT

Work described herein has been supported, in part, by Public Health Service Research Grants EY08426, P50HG00835 and HG00457. The U.S. Government may therefore have certain rights in the invention.

2. BACKGROUND OF THE INVENTION

In the United States, glaucoma is the second leading cause of legal blindness overall and the leading cause of blindness in African-American individuals (Hiller, R and H. A. Kahn, (1975) *Am. J. Ophthalmol* 80: 62 and Kahn, H. A. and H. B. Moorhead (1973) *US Public Health Service Publication* NIH73-427, 120). Primary open glaucoma (POAG) is the most common form of glaucoma affecting 1–2% of the population over age forty (J. M. Tielsch et al., (1990) *Arch Ophthalmol.* 108: 286). Nearly 12,000 people in the United States are blinded annually by this disorder (H. B. Moorhead (1973) *US Public Health Service Publication* NIH73-427, 1202–4; J. M. Tielsch et al., (1990) *Arch Ophthalmol.* 108: 286 and J. M. Tielsch, in *Transactions of the New Orleans Academy of Ophthalmology,* Ball, S. F. Franklin R. M., Eds (Kugler, Amsterdam, 1993), pp61–68).

One method of identifying genes involved in multifactorial disorders is to study Mendelian diseases with a similar phenotype. Juvenile open angle glaucoma (JOAG) is a term used to refer to a subset of POAG which has an earlier age of onset and a highly penetrant autosomal dominant mode of inheritance (A. T. Johnson et al., (1993) *Ophthalmology* 100:524). On clinical examination, patients with juvenile onset open angle glaucoma are identical to patients with later onset disease in that both exhibit elevated intraocular pressure and optic nerve cupping in the presence of a biomicroscopically normal trabecular meshwork. Isolation of genes involved in JOAG are needed to develop therapeutics and diagnostics for glaucoma.

2. SUMMARY OF THE INVENTION

In one aspect, the invention features isolated GLC1A nucleic acid molecules. The disclosed molecules can be non-coding, (e.g. probe, antisense or ribozyme molecules) or can encode a functional polypeptide (e.g. a polypeptide which specifically modulates, e.g., by acting as either an agonist or antagonist, at least one bioactivity of the human GLC1A polypeptide).

In further embodiments, the nucleic acid molecule is a GLC1A nucleic acid that is at least 70%, preferably 80%, more preferably 85%, and even more preferably at least 95% homologous in sequence to the nucleic acids shown as SEQ ID Nos: 1 or 2 or to the complement of the nucleic acids shown as SEQ ID Nos: 1 or 2. In another embodiment, the nucleic acid molecule encodes a polypeptide that is at least 92% and more preferably at least 95% similar in sequence to the polypeptide shown in SEQ ID No: 3.

The invention also provides probes and primers comprising substantially purified oligonucleotides, which correspond to a region of nucleotide sequence which hybridizes to at least 6 consecutive nucleotides of the sequences set forth as SEQ ID Nos: 1 or 2 or complements of the sequences set forth as SEQ ID Nos: 1 or 2, or naturally occurring mutants thereof In preferred embodiments, the probe/primer further includes a label group attached thereto, which is capable of being detected.

For expression, the subject GLC1A nucleic acids can include a transcriptional regulatory sequence, e.g. at least one of a transcriptional promoter (e.g., for constitutive expression or inducible expression) or transcriptional enhancer or suppressor sequence, which regulatory sequence is operably linked to the GLC1A gene sequence. Such regulatory sequences in conjunction with a GLC1A nucleic acid molecule can be useful vectors for gene expression. This invention also describes host cells transfected with said expression vector whether prokaryotic or eukaryotic and in vitro (e.g. cell culture) and in vivo (e.g. transgenic) methods for producing GLC1A proteins by employing said expression vectors.

In another aspect, the invention features isolated GLC1A polypeptides, preferably substantially pure preparations e.g. of plasma purified or recombinantly produced GLC1A polypeptides. In one embodiment, the polypeptide is identical to or similar to a GLC1A protein represented in SEQ ID No: 3. Related members of the vertebrate and particularly the mammalian GLC1A family are also within the scope of the invention. Preferably, a GLC1A polypeptide has an amino acid sequence at least about 92% homologous and preferably at least about 95%, 96%, 97%, 98% or 99% homologous to the polypeptide represented in SEQ ID No: 3. In a preferred embodiment, the GLC1A polypeptide that is encoded by a nucleic acid which hybridizes with a nucleic acid sequence represented in one of SEQ ID Nos: 1 or 2. The subject GLC1A proteins also include modified protein, which are resistant to post-translational modification, as for example, due to mutations which alter modification sites (such as tyrosine, threonine, serine or aspargine residues), or which prevent glycosylation of the protein, or which prevent interaction of the protein with intracellular proteins involved in signal transduction.

The GLC1A polypeptide can comprise a full length protein, such as represented in SEQ ID No: 3, or it can comprise a fragment corresponding to one or more particular motifs/domains, or to arbitrary sizes, e.g., at least 5, 10, 25, 50, 100, 150, 175, 200, 225, 250,275, 300, 325, 350, 375, 400, 425, 450, 475, 480, 485, 490, 495, or 500 amino acids in length.

Another aspect of the invention features chimeric molecules (e.g. fusion proteins) comprised of a GLC1A protein. For instance, the GLC1A protein can be provided as a recombinant fusion protein which includes a second polypeptide portion, e.g., a second polypeptide having an amino acid sequence unrelated (heterologous) to the GLC1A polypeptide (e.g. the second polypeptide portion is glutathione-S-transferase, an enzymatic activity such as alkaline phosphatase or an epitope tag).

Yet another aspect of the present invention concerns an immunogen comprising a GLC1A polypeptide in an immunogenic preparation, the immunogen being capable of eliciting an immune response specific for a GLC1A polypeptide; e.g. a humoral response, an antibody response and/or cellular response. In preferred embodiments, the immunogen comprises an antigenic determinant, e.g. a unique determinant, from the protein represented in SEQ ID No: 3.

A still further aspect of the present invention features antibodies and antibody preparations specifically reactive with an epitope of the GLC1A protein. In preferred embodiments the antibody specifically binds to at least one epitope represented in SEQ ID No: 3.

The invention also features transgenic non-human animals which include (and preferably express) a heterologous form of a GLC1A gene described herein, or which misexpress an endogenous GLC1A gene (e.g., an animal in which expression of one or more of the subject GLC1A proteins is disrupted). Such a transgenic animal can serve as an animal model for studying cellular and tissue disorders comprising mutated or mis-expressed GLC1A alleles or for use in drug screening. Alternatively, such a transgenic animal can be useful for expressing recombinant GLC1A polypeptides.

In yet another aspect, the invention provides assays, e.g., for screening test compounds to identify inhibitors, or alternatively, potentiators, of an interaction between a GLC1A protein and, for example, a virus, an extracellular ligand of the GLC1A protein, or an intracellular protein which binds to the GLC1A protein. An exemplary method includes the steps of (i) combining a GLC1A polypeptide or bioactive fragments thereof, a GLC1A target molecule (such as a GLC1A ligand or a GLC1A substrate), and a test compound, e.g., under conditions wherein, but for the test compound, the GLC1A protein and target molecule are able to interact; and (ii) detecting the formation of a complex which includes the GLC1A protein and the target polypeptide either by directly quantitating the complex, by measuring inductive effects of the GLC1A protein, or, in the instance of a substrate, measuring the conversion to product. A statistically significant change, such as a decrease, in the interaction of the GLC1A and target molecule in the presence of a test compound (relative to what is detected in the absence of the test compound) is indicative of a modulation (e.g., inhibition or potentiation of the interaction between the GLC 1A protein and the target molecule).

Yet another aspect of the present invention concerns a method for modulating GLC1A bioactivity, (e.g., by potentiating or disrupting a GLC1A bioactivity). In general, whether carried out in vivo, in vitro, or in situ, the method comprises treating the cell with an effective amount of a GLC1A therapeutic so as to alter, relative to the cell in the absence of treatment, a GLC1A bioactivity. Accordingly, the method can be carried out with GLC1A therapeutics such as peptide and peptidomimetics or other molecules identified in the above-referenced drug screens which agonize or antagonize the effects of GLC1A (e.g., signalling from a GLC1A protein or ligand binding of a GLC1A protein). Other GLC1A therapeutics include antisense constructs for inhibiting expression of GLC1A proteins, and dominant negative mutants of GLC1A proteins which competitively inhibit ligand interactions upstream and signal transduction downstream of the wild-type GLC1A protein.

A further aspect of the present invention provides a method of determining if a subject is at risk for glaucoma or other disorder resulting from a mutant GLC1A gene. The method includes detecting, in a tissue of the subject, the presence or absence of a genetic lesion characterized by at least one of (i) a mutation of a gene encoding a GLC1A protein, e.g., a gene represented in one of SEQ ID Nos: 1 or 2 or a homolog thereof; or (ii) the mis-expression of a GLC1A gene. In preferred embodiments, detecting the genetic lesion includes ascertaining the existence of at least one of: a deletion of one or more nucleotides from a GLC1A gene; an addition of one or more nucleotides to the gene, a substitution of one or more nucleotides of the gene, a gross chromosomal rearrangement of the gene; an alteration in the level of a messenger RNA transcript of the gene (e.g., due to a promoter mutation); the presence of a non-wild type splicing pattern of a messenger RNA transcript of the gene; a non-wild type level of the protein; and/or an aberrant level of soluble GLC1A protein.

For example, detecting the genetic lesion can include (i) providing a probe/primer comprised of an oligonucleotide which hybridizes to a sense or antisense sequence of a GLC1A gene or naturally occurring mutants thereof, or 5' or 3' flanking sequences naturally associated with the GLC1A gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the GLC1A gene and, optionally, of the flanking nucleic acid sequences. For instance, the primer can be employed in a polymerase chain reaction (PCR) or in a ligation chain reaction (LCR). In alternate embodiments, the level of a GLC1A protein is detected in an immunoassay using an antibody which is specifically immunoreactive with the GLC1A protein.

Other features and advantages of the invention will be apparent from the following detailed description and claims.

3. BRIEF DESCRIPTION OF THE FIGURES

FIG. 1 is a DNA sequence of the human GLC1A gene including two intron sequences and the 5' and 3' untranslated regions (UTRs) (SEQ. ID. No. 1). DNA encoding protein and comprising the three exon sequences is provided as SEQ. ID. No. 2. The encoded protein is presented as SEQ. ID. No. 3.

FIG. 2 shows the Yeast Artificial Chromosomes (YACS) comprising the minimum tiling path contigs. Solid circles indicate the position of markers (STSs), which were shown to be contained within each YAC. Disease intervals based on recombination within families and shared haplotypes between families are indicated with brackets.

FIGS. 3A and B shows two polymerase chain reaction (PCR) amplimers of the GLC1A gene found to harbor sequence changes in patients with glaucoma.

Figure 4:
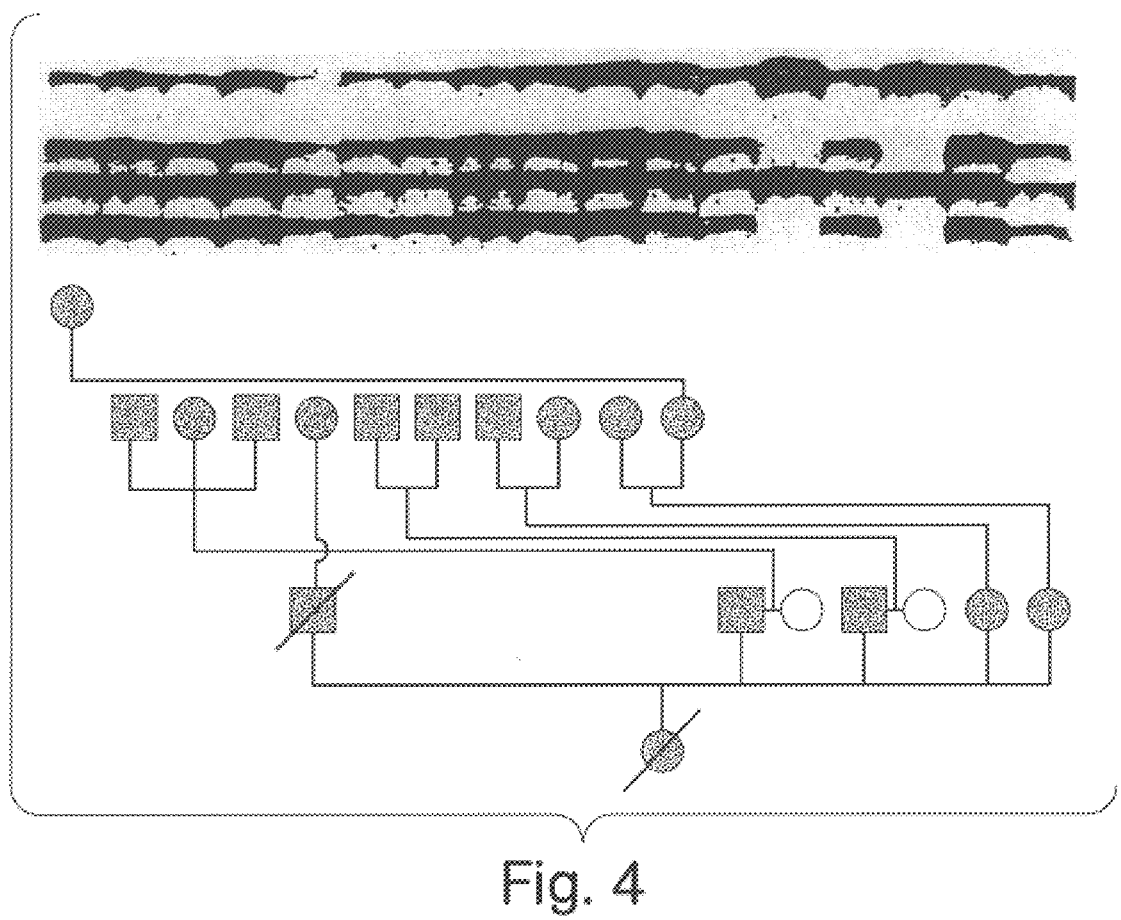
Figure 5A:
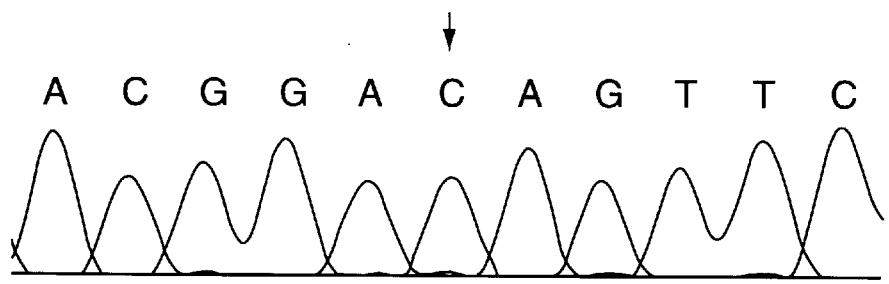
Figure 5B:
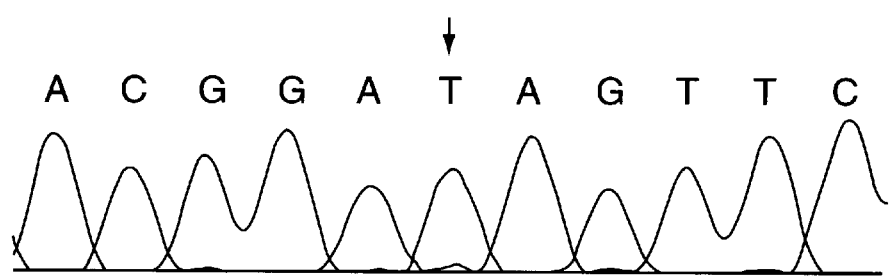
Figure 5C:
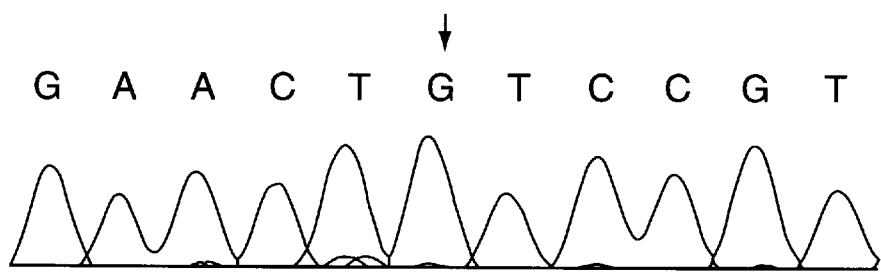
Figure 5D:
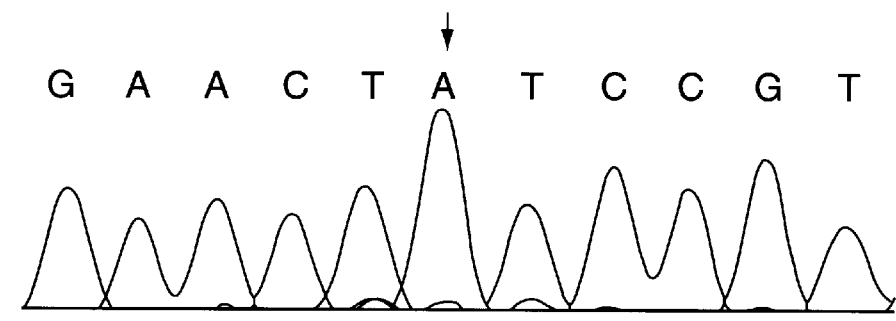

FIG. 4 schematically depicts the segregation of the GLY364VAL mutation in a four generation family affected with open angle glaucoma. Black symbols in the pedigree drawing indicate individuals with documented evidence of open angle glaucoma. White symbols indicate spouses that are clinically unaffected. A photograph of a silver-stained SSCP gel is shown below the pedigree drawing and is aligned so that each gel lane lies directly below the pedigree symbol of the family member whose DNA was analyzed in that lane. For simplicity, clinically unaffected family members were not included.

FIGS. 5A–D is a representative chromatogram generated by fluorescent dye-primer sequencing of cloned PCR amplification products from an affected individual reveals a C to T transition which would be expected to result in a premature stop at codon 368 (GLN368STOP). Sequences in the forward and reverse directions for both the mutant and normal genes are shown: (A) normal, forward; (B) mutant, forward; (C) normal, reverse; (D) mutant, reverse.

4. DETAILED DESCRIPTION OF THE INVENTION

4.1. General

As reported herein, a genetic locus associated with JOAG was identified on chromosome 1q21–q31 by genetic linkage analysis. Observed recombinations between the glaucoma phenotype and highly polymorphic genetic markers in two large JOAG kindreds allowed the interval containing GLC1A gene to be narrowed to a 3 cM region of chromosome 1q between markers D1S3665 and D1S3664. Further evaluation of marker haplotypes revealed that each of three pairs of glaucoma families shared alleles of the same eight contiguous markers suggesting that the GLC1A gene lies within a narrower interval defined by D1S1619 and D1S3664.

Several genes mapping to the GLC1A region of chromosome 1 were considered as candidates for the disease-causing gene. Three genes (LAMC1 (H. C. Watkins et. al., (1993) *Hum. Mol. Genet.* 2: 1084), NPRI (D. G. Lowe et al., (1990) *Genomics* 8:304), and CNR2 (S. Munro et al., (1993) *Nature* 365:61), were excluded from the candidate region by genetic linkage analysis using intragenic polymorphic markers. Five additional candidate genes were determined to lie within the observed recombinant interval by YAC STS content mapping: selectin E (M. P. Bevilacqua et al., (1989) *Science* 243:1160) (GenBank accession no. M24736); selectin L (T. F. Tedder et al., (1989) *J. Exp. Med.* 170:123) (GenBank accession no. M25280); TXGP-1 (S. Miura et al., (1991) *Mol. Cell Biol* 11:1313) (GenBank accession no. MD90224; APT1LG1 (T. Takahashi et al., (1994) *Int. Immunol.* 6, 1567); and TIGR (Trabecular meshwork Induced Glucocorticoid Response Protein) (J. R. Polansky et al., (1989) *Prog. Clin. Biol. Res* 12:113; J. Escribano et al., (1995) *J. Biochem.* 118:921; International Patent Application Publication No. WO 96/14411 ) (GenBank accession nos. R95491, R95447, R95443, R47209). However, two of these genes (selectin E, and selectin L) were found to lie outside of the shared haplotype interval with this approach. The remaining genes (APT1LG1, TXGP-1, and TIGR) were found to map within the narrowest JOAG interval by both YAC STS content and radiation hybrid mapping.

Two of these genes (APT1LG1 and TIGR) were screened for mutations in families with JOAG. Primers were selected from the available sequence (T. Takahashi et al., (1994) *Int. Immunol.* 6, 1567, J. Escribano et al., (1995) *J. Biochem.* 118:921; International Patent Application Publication No. WO 96/14411) (GenBank accession nos. R95491, R95447, R95443, R47209) and overlapping PCR amplification products were evaluated by single strand conformation polymorphism analysis (B. J. Bassam et al., (1991) *Anal. Biochem.* 196: 80) and direct DNA sequencing. Although the complete cDNA sequence of the APT1LG1 and TIGR genes have been published, the presence of intervening sequences permitted only 85–90% of their coding sequences to be screened in genomic DNA. Eight unrelated JOAG patients were screened with the APT1LG1 assay but no sequence variants were identified.

The TIGR gene assay was initially used to screen affected members of four different 1q-linked glaucoma families, and affected members of four smaller families implicated by haplotypic data. Amino-acid-altering mutations were detected in four of eight families. A tyrosine to histidine mutation in codon 437 (FIGS. 3A and 4) was detected in all 22 affected members of the original family (V. C. Sheffield et al., (1993) *Nature Genet.* 4:47) linked to 1q. A glycine to valine mutation in codon 364 (FIG. 3B) was detected in two families including one previously unreported adult-onset open angle glaucoma family with 15 affected members (FIG. 4). A nonsense mutation (glutamine to stop) at codon 368 (FIGS. 3B and 5) was detected in two families. The latter mutation would be expected to result in a truncation of the gene product.

The prevalence of mutations in the two PCR amplimers that harbored these three changes was then estimated by screening four different populations: glaucoma patients with a family history of the disease; unselected primary open angle glaucoma probands seen in a single clinic; the general population (approximated by patients with heritable retinal disease and spouses from families who participated in prior linkage studies); and, unrelated volunteers over the age of 40 with normal intraocular pressures and no personal or family history of glaucoma. PCR products determined to contain a sequence variation by SSCP were sequenced and compared to sequence generated from an unaffected individual as well as the normal chromosome in each affected individual. Overall, missense or nonsense mutations were found in about 3–5% of unrelated glaucoma patients and in about 0.2% of controls. A Chi-square test revealed this difference to be significant (p<0.001). Table 1 sets forth GLC1A mutations and polymorphisms identified to date.

TABLE 1

Mutations

1. GLN368STOP
2. GLY364VAL
3. TYR437HIS
4. ILE477ASN
5. 6 bp insertion in codon 396
6. VAL495ILE
7. ALA445VAL
8. THR377MET
9. GLN19HIS
10. ARG82CYS Polymorphisms

1. TYR347TYR
2. THR325THR
3. VAL439VAL
4. LYS398ARG
5. PRO13PRO

In summary, genetic linkage analysis and examination of shared haplotypes was used to narrow the 1q glaucoma disease interval. A gene that lies within this interval and which is known to be expressed in the ciliary body (J. Escribano et al., (1995) *J. Biochem* 118:921) and trabecular meshwork (J. R. Polansky et al., (1989) *Prog. Clin. Biol. Res* 12:113 and International Patent Application Publication No. WO 96/14411) was examined. 13 unrelated patients with glaucoma (including the proband of the family (V. C. Sheffield et al., (1993) *Nature Genet.* 4:47) whose glaucoma phenotype was originally linked to 1q) who each harbored one of three different amino-acid-altering mutations were identified. Collectively, this is compelling evidence that mutations in this gene are responsible for the glaucoma previously linked to chromosome 1q. In addition, the discovery of a mutation in 15 affected members of an adult-onset family as well as the identification of mutations in 2.9% of a consecutively ascertained group of unselected open angle glaucoma patients, suggests that this gene plays a role in a portion of all open angle glaucoma. It is possible that more than 3% of open angle glaucoma will eventually be shown to be associated with mutations in this gene for two reasons: 1) only a portion of the gene was evaluated in this study; and, 2) the screening methods used are not 100% sensitive.

The gene, mutations in which have been linked to the glaucoma phenotype, was sequenced using standard techniques. The DNA sequence, including 5' and 3' untranslated regions and two intron sequences is shown in FIG. 1. Importantly, this sequence differs substantially from the TIGR gene sequence reported in International Patent Application No. WO 96/14411 (GenBank accession nos. R95491, R95447, R95443 and R947209). In fact, as reported, the TIGR gene sequence does not encode a functional protein.

A summary of the differences between the GLC1A gene disclosed herein, and the TIGR gene are presented in Table 2.

TABLE 2

1. The "C" at bp #331 of the GLC1A DNA coding sequence (FIG. 1) is not present in the TIGR sequence.

2. The 29 bps "AGGGGCTGCAGAGG-GAGCTGGGCACCCTG" (SEQ ID NO. 8) at bp #344–372 of the GLC1A DNA coding sequence are not included in the TIGR sequence.

Errors 1 and 2 cause the TIGR sequence to wrongly predict 4 amino acids and exclude 10 amino acids from the protein sequence.

3. The "C" at bp #559 of the GLC1A DNA coding sequence is not present in the TIGR sequence.
4. A "T" is wrongly inserted between bp #560 and #561 of the GLC1A DNA coding sequence in the TIGR sequence.

Errors 3 and 4 cause the TIGR sequence to incorrectly predict a serine amino acid at residue #187 instead of a glutamine.

5. The 9 bps "CTCAGGAGT" present at bps 706–714 of the GLC1A DNA coding sequence are wrongly duplicated and inserted between bp 714 and 715 in the TIGR sequence.

Consequently, the TIGR DNA sequence incorrectly predicts that 3 amino acids are inserted into the GLC1A protein sequence.

6. A "T" is incorrectly inserted between bp #841 and #842 of the GLC1A DNA coding sequence in the TIGR sequence.
7. The "G" at bp #891 of the GLC1A DNA coding sequence is not present in the TIGR sequence.

Errors 6 and 7 cause 17 amino acids predicted by the GLC1A DNA coding sequence to be out of frame in the TIGR sequence.

8. A "G" at bp #979 of the GLC1A DNA coding sequence is replaced with a "C" in the TIGR sequence.
9. A "C" at bp #980 of the GLC1A DNA coding sequence is replaced with a "G" in the TIGR sequence.

Errors 8. and 9. cause the TIGR sequence to wrongly predict an arginine amino acid at residue #327 instead of an alanine. The above 9 errors in the TIGR GLC1A sequence cause 42 incorrect amino acid predictions.

The identification of this disease gene increases the understanding of the pathophysiology of glaucoma, which in turn facilitates the development of assays for identifying molecules that modulate (e.g. agonize or antagonize) the bioactivity of a functional or mutant TIGR gene or protein. A therapeutically effective amount of these molecules can be administered to a subject with glaucoma or at risk for developing glaucoma to prevent or reduce the severity of the condition.

4.2 Definitions

For convenience, the meaning of certain terms and phrases employed in the specification, examples, and appended claims are provided below.

The term "agonist", as used herein, is meant to refer to an agent (e.g., a GLC1A therapeutic) that directly or indirectly enhances, supplements or potentiates a GLC1A bioactivity.

The term "antagonist", as used herein, is meant to refer to an agent (e.g. a GLC1A therapeutic) that directly or indirectly prevents, minimizes or suppresses a GLC1A bioactivity.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-GLC1A-Y, wherein GLC1A represents a portion of the protein which is derived from one of the GLC1A proteins, and X and Y are independently absent or represent amino acid sequences which are not related to one of the GLC1A sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a gg polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the polypeptides of the present invention, including both exon and (optionally) intron sequences. A "recombinant gene" refers to nucleic acid encoding a GLC1A polypeptide and comprising GLC1A-encoding exon sequences, though it may optionally include intron sequences which are either derived from a chromosomal GLC1A gene or from an unrelated chromosomal gene. Exemplary recombinant genes encoding the subject GLC1A polypeptides are represented in the appended Sequence Listing. The term "intron" refers to a DNA sequence present in a given GLC1A gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the GLC1A sequences of the present invention.

The term "interact" as used herein is meant to include detectable interactions between molecules, such as can be detected using, for example, a yeast two hybrid assay. The term interact is also meant to include "binding" interactions between molecules. Interactions may, for example, be protein-protein or protein-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject GLC1A polypeptides preferably includes no more than 10 kilobases (kb) of nucleic acid sequence which naturally immediately flanks the GLC1A gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, (i.e., activation or stimulation), for example by agonizing; and downregulation, (i.e. inhibition or suppression) for example by antagonizing or a GLC1A bioactivity.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant GLC1A genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a GLC1A polypeptide is inserted into a suitable expression vector which is in turn used to transform a host cell to produce the heterologous protein. Moreover, the phrase "derived from", with respect to a recombinant GLC1A gene, is meant to include within the meaning of "recombinant protein" those proteins having an amino acid sequence of a native GLC1A protein, or an amino acid sequence similar thereto which is generated by mutations including substitutions and deletions (including truncation) of a naturally occurring form of the protein.

"Small molecule" as used herein, is meant to refer to a composition, which has a molecular weight of less than about 5 kD and most preferably less than about 4 kD. Small molecules can be nucleic acids, peptides, polypeptides, peptidometics, carbohydrates, lipids or other organic carbon containing or inorganic molecules. Extensive libraries of chemical or biological (e.g., fungal, bacterial or algal extracts) mixtures are available for screening with the assays of the invention.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400, 450, 500, 550, 600, 650, 700, 750, 800, 850, 900, 950, 1000, 1050, 1100, 1150, 1200, 1250, 1300, 1350, 1400, 1450, 1460, 1470, 1480, 1490 consecutive nucleotides of a vertebrate, preferably GLC1A gene, such as a GLC1A sequence designated in one of SEQ ID Nos: 1 or 2, or a sequence complementary thereto, or naturally occurring mutants thereof, such that it shows at least 10 times more hybridization, preferably at least 50 times more hybridization, and even more preferably at least 100 times more hybridization than it does to a cellular nucleic acid (e.g., mRNA or genomic DNA) encoding a protein other than a vertebrate GLC1A protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant GLC1A genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of GLC1A proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian GLC1A polypeptide or, in the case of anti-sense expression from the transferred gene, the expression of a naturally-occurring form of the GLC1A protein is disrupted.

As used herein, the term "transgene" means a nucleic acid sequence (encoding, e.g., one of the mammalian GLC1A polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the GLC1A proteins, e.g. either agonistic or antagonistic forms. However, transgenic animals in which the recombinant GLC1A gene is silent are also contemplated, as for example, the FLP or CRE recombinase dependent constructs described below. Moreover, "transgenic animal" also includes those recombinant animals in which gene disruption of one or more GLC1A genes is caused by human intervention, including both recombination and antisense techniques.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding GLC1A polypeptides, and/or equivalents of such nucleic acids. The term equivalent is understood to include nucleotide sequences encoding functionally equivalent GLC1A polypeptides or functionally equivalent peptides having an activity of a vertebrate GLC1A protein such as described herein. Equivalent nucleotide sequences will include sequences that differ by one or more nucleotide substitutions, additions or deletions, such as allelic variants; and will, therefore, include sequences that differ from the nucleotide sequence of the GLC1A gene shown in SEQ ID Nos: 1 or 2 due to the degeneracy of the genetic code.

Preferred nucleic acids are vertebrate GLC1A nucleic acids. Particularly preferred vertebrate GLC1A nucleic acids are mammalian. Regardless of species, particularly preferred GLC1A nucleic acids encode polypeptides that are at least 90% similar to an amino acid sequence of human GLC1A. Preferred nucleic acids encode a GLC1A polypeptide comprising an amino acid sequence at least 90% homologous and more preferably 94% homologous with an amino acid sequence of a vertebrate GLC1A, e.g., such as a sequence shown in one of SEQ ID Nos: 1 or 2. Nucleic acids which encode polypeptides at least about 95%, and even more preferably at least about 98–99% similarity with an amino acid sequence represented in SEQ ID Nos.: 1 or 2 are also within the scope of the invention. In a particularly preferred embodiment, the nucleic acid of the present invention encodes an amino acid GLC1A sequence shown in one of SEQ ID No: 2. In one embodiment, the nucleic acid is a cDNA encoding a peptide having at least one bioactivity of the subject GLC1A polypeptide. Preferably, the nucleic acid includes all or a portion of the nucleotide sequence corresponding to the coding region of SEQ ID Nos: 1 or 2.

Still other preferred nucleic acids of the present invention encode a GLC1A polypeptide which includes a polypeptide sequence corresponding to all or a portion of amino acid residues of SEQ ID No: 2 e.g., at least 2, 5, 10, 25, 50, 100, 150 or 200 amino acid residues of that region. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 200, 250, 300, 350, 400, 410, 420, 430, 435 or 440 base pairs.

Another aspect of the invention provides a nucleic acid which hybridizes to a nucleic acid represented by one of SEQ ID Nos: 1 or 2 Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a GLC1A nucleic acid of the present invention will bind to one of SEQ ID Nos 1 or 2 under moderately stringent conditions, for example at about 2.0×SSC and about 40° C. In a particularly preferred embodiment, aGLC1A nucleic acid of the present invention will bind to one of SEQ ID Nos: 1, 3 or 4 under high stringency conditions, but will not bind to the nucleic acids shown in SEQ ID Nos: 6, 8, 9 or 11.

Preferred nucleic acids have a sequence at least 75% homologous and more preferably 80% and even more preferably at least 85% homologous with an amino acid sequence of a mammalian GLC1A, e.g., such as a sequence shown in one of SEQ ID Nos: 1 and 2 Nucleic acids at least 90%, more preferably 95%, and most preferably at least about 98–99% homologous with a nucleic sequence represented in one of SEQ ID Nos: 1 and 2 are of course also within the scope of the invention. In preferred embodiments, the nucleic acid is a mammalian GLC1A gene and in particularly preferred embodiments, includes all or a portion of the nucleotide sequence corresponding to the coding region of one of SEQ ID Nos: 1 or 2.

Nucleic acids having a sequence that differs from the nucleotide sequences shown in one of SEQ ID Nos: 1 or 2 due to degeneracy in the genetic code are also within the scope of the invention. Such nucleic acids encode functionally equivalent peptides (i.e., a peptide having a biological activity of a GLC1A polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a GLC1A polypeptide. However, it is expected that DNA sequence polymorphisms that do lead to changes in the amino acid sequences of the subject GLC1A polypeptides will exist among mammalians. One skilled in the art will appreciate that these variations in one or more nucleotides (e.g., up to about 3–5% of the nucleotides) of the nucleic acids encoding polypeptides having an activity of a mammalian GLC1A polypeptide may exist among individuals of a given species due to natural allelic variation.

As indicated by the examples set out below, GLC1A protein-encoding nucleic acids can be obtained from mRNA present in any of a number of eukaryotic cells. It should also be possible to obtain nucleic acids encoding mammalian GLC1A polypeptides of the present invention from genomic DNA from both adults and embryos. For example, a gene encoding a GLC1A protein can be cloned from either a cDNA or a genomic library in accordance with protocols described herein, as well as those generally known to persons skilled in the art. Examples of tissues and/or libraries suitable for isolation of the subject nucleic acids include ocular tissue, among others. A cDNA encoding a GLC1A protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian GLC1A protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos: 1 and 2.

4.3.1. Vectors

This invention also provides expression vectors containing a nucleic acid encoding a GLC1A polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject mammalian GLC1A proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject GLC1A polypeptide, or alternatively, encoding a peptide which is an antagonistic form of the GLC1A protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject GLC1A proteins. Thus, another aspect of the invention features expression vectors for in vivo or in vitro transfection and expression of a GLC1A polypeptide in particular cell types so as to reconstitute the function of, or alternatively, abrogate the function of GLC1A-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject GLC1A polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject GLC1A polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of GLC1A genes from mammalian organisms will further allow for the generation of probes and primers designed for use in identifying and/or cloning GLC1A homologs in other cell types, e.g. from other tissues, as well as GLC1A homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID No:1 and 2, or naturally occurring mutants thereof. For instance, primers based on the nucleic acid represented in SEQ ID Nos:1 and 2 can be used in PCR reactions to clone GLC1A homologs. Preferred primers of the invention are set forth as SEQ ID Nos. 4 and 5; and SEQ ID Nos. 5 and 6.

Likewise, probes based on the subject GLC1A sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

As discussed in more detail below, such probes can also be used as a part of a diagnostic test kit for identifying cells or tissue which misexpress a GLC1A protein, such as by measuring a level of a GLC1A -encoding nucleic acid in a sample of cells from a patient; e.g. detecting GLC1A mRNA levels or determining whether a genomic GLC1A gene has been mutated or deleted. Briefly, nucleotide probes can be generated from the subject GLC1A genes which facilitate histological screening of intact tissue and tissue samples for the presence (or absence) of GLC1A-encoding transcripts. Similar to the diagnostic uses of anti-GLC1A antibodies, the use of probes directed to GLC1A messages, or to genomic GLC1A sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described herein, the oligonucleotide probes can help facilitate the determination of the molecular basis for a developmental disorder which may involve some abnormality associated with expression (or lack thereof) of a GLC1A protein. For instance, variation in polypeptide synthesis can be differentiated from a mutation in a coding sequence.

4.3.3. Antisense, Ribozyme and Triplex Techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject GLC1A proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a GLC1A protein. Alternatively, the antisense construct is an oligonucleotide probe which is generated ex vivo and which, when introduced into the cell causes inhibition of expression by hybridizing with the mRNA and/or genomic sequences of a GLC1A gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the GLC1A nucleotide sequence of interest, are preferred.

Antisense approaches involve the design of oligonucleotides (either DNA or RNA) that are complementary to GLC1A mRNA. The antisense oligonucleotides will bind to the GLC1A mRNA transcripts and prevent translation. Absolute complementarity, although preferred, is not required a sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of a GLC1A gene could be used in an antisense approach to inhibit translation of endogenous GLC1A mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of GLC1A mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, *Proc. Natl. Acad Sci. U.S.A.* 86:6553–6556; Lemaitre et al., 1987, *Proc. Natl. Acad. Sci.* 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al., 1988, *BioTechniques* 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an -anomeric oligonucleotide. An -anomeric oligonucleotide forms specific double-stranded hybrids with complementary RNA in which, contrary to the usual-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad Sci. U.S.A.* 85:7448–7451), etc.

While antisense nucleotides complementary to the GLC1A coding region sequence could be used, those complementary to the transcribed untranslated region are most preferred.

The antisense molecules should be delivered to cells which express the GLC1A in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous GLC1A transcripts and thereby prevent translation of the GLC1A mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad Sci. U.S.A.* 78:1441–1445), the regulatory sequences of the metallothionein gene (Brinster et al, 1982, *Nature* 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave GLC1A mRNA transcripts can also be used to prevent translation of GLC1A mRNA and expression of GLC1A. (See, e.g., PCT International Publication WO 90/11364, published Oct. 4, 1990; Sarver et al., 1990, *Science* 247:1222–1225). While ribozymes that cleave mRNA at site specific recognition sequences can be used to destroy GLC1A mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature,* 334:585–591. There are hundreds of potential hammerhead ribozyme cleavage sites within the nucleotide sequence of human GLC1A cDNA. Preferably the ribozyme is engineered so that the cleavage recognition site is located near the 5' end of the GLC1A mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, *Science,* 224:574–578; Zaug and Cech, 1986, *Science,* 231:470–475; Zaug, et al., 1986, *Nature,* 324:429–433; published International patent application No. WO 88/04300 by University Patents Inc.; Been and Cech, 1986, *Cell,* 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in GLC1A.

As in the antisense approach, the ribozymes can be composed of modified oligonucleotides (e.g. for improved stability, targeting, etc.) and should be delivered to cells which express the GLC1A in vivo e.g., hypothalamus and/or the choroid plexus. A preferred method of delivery involves using a DNA construct "encoding" the ribozyme under the control of a strong constitutive pol III or pol II promoter, so that transfected cells will produce sufficient quantities of the ribozyme to destroy endogenous GLC1A messages and inhibit translation. Because ribozymes unlike antisense molecules, are catalytic, a lower intracellular concentration is required for efficiency.

Endogenous GLC1A gene expression can also be reduced by inactivating or "knocking out" the GLC1A gene or its promoter using targeted homologous recombination. (E.g., see Smithies et al., 1985, *Nature* 317:230–234; Thomas & Capecchi, 1987, *Cell* 51:503–512; Thompson et al., 1989 *Cell* 5:313–321; each of which is incorporated by reference herein in its entirety). For example, a mutant, non-functional GLC1A (or a completely unrelated DNA sequence) flanked by DNA homologous to the endogenous GLC1A gene (either the coding regions or regulatory regions of the GLC1A gene) can be used, with or without a selectable marker and/or a negative selectable marker, to transfect cells that express GLC1A in vivo. Insertion of the DNA construct, via targeted homologous recombination, results in inactivation of the GLC1A gene. Such approaches are particularly suited in the agricultural field where modifications to ES (embryonic stem) cells can be used to generate animal offspring with an inactive GLC1A (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous GLC1A gene expression can be reduced by targeting deoxyribonucleotide sequences complementary to the regulatory region of the GLC1A gene (i.e., the GLC1A promoter and/or enhancers) to form triple helical structures that prevent transcription of the GLC1A gene in target cells in the body. (See generally, Helene, C. 1991, *Anticancer Drug Des.,* 6(6):569–84; Helene, C., et al., 1992, Ann, N.Y. *Acad. Sci.,* 660:27–36; and Maher, L. J., 1992, *Bioassays* 14(12):807–15).

Likewise, the antisense constructs of the present invention, by antagonizing the normal biological activity of one of the GLC1A proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to aGLC1AmRNA or gene sequence) can be used to investigate role of GLC1A in developmental events, as well as the normal cellular function of GLC1A in adult tissue. Such techniques can be utilized in cell culture, but can also be used in the creation of transgenic animals, as detailed below.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding GLC1A proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. Polypeptides of the Present Invention

The present invention also makes available isolated GLC1A polypeptides which are isolated from, or otherwise substantially free of other cellular proteins, especially other signal transduction factors and/or transcription factors which may normally be associated with the GLC1A polypeptide. The term "substantially free of other cellular proteins" (also referred to herein as "contaminating proteins") or "substantially pure or purified preparations" are defined as encompassing preparations of GLC1A polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified GLC1A preparations will lack any contaminating proteins from the same animal from which GLC1A is normally produced, as can be accomplished by recombinant expression of, for example, a human GLC1A protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated GLC1A polypeptides can include all or a portion of an amino acid sequences corresponding to a GLC1A polypeptide represented in SEQ ID No: 3 Isolated peptidyl portions of GLC1A proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a GLC1A polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") GLC1A protein.

Another aspect of the present invention concerns recombinant forms of the GLC1A proteins. Recombinant polypeptides preferred by the present invention, in addition to native GLC1A proteins, are at least 92% homologous and more preferably 94% homologous and most preferably 95% homologous with an amino acid sequence represented by SEQ ID Nos: 3. Polypeptides which are at least about 98–99% homologous with a sequence selected from the group consisting of SEQ ID No: 3 are also within the scope of the invention. In a preferred embodiment, a GLC1A protein of the present invention is a GLC1A protein. In a particularly preferred embodiment a GLC1A protein comprises the coding sequence of one of SEQ ID No.: 3. In particularly preferred embodiments, a GLC1A protein has a GLC1A bioactivity.

The present invention further pertains to recombinant forms of one of the subject GLC1A polypeptides which are encoded by genes derived from a mammalian organism, and which have amino acid sequences evolutionarily related to the GLC1A proteins represented in SEQ ID Nos: 3. Such recombinant GLC1A polypeptides preferably are capable of functioning in one of either role of an agonist or antagonist of at least one biological activity of a wild-type ("authentic") GLC1A protein of the appended sequence listing. The term "evolutionarily related to", with respect to amino acid sequences of GLC1A proteins, refers to both polypeptides having amino acid sequences which have arisen naturally, and also to mutational variants of GLC1A polypeptides which are derived, for example, by combinatorial mutagenesis. Such evolutionarily derived GLC1A polypeptides preferred by the present invention have a GLC1A bioactivity and are at least 92% homologous and more preferably 94% homologous and most preferably 98–99% homologous with the amino acid sequence selected from the group consisting of SEQ ID Nos: 3. In a particularly preferred embodiment, a GLC1A protein comprises the amino acid coding sequence of SEQ ID No: 3.

In general, polypeptides referred to herein as having an activity (e.g., are "bioactive") of a GLC1A protein are defined as polypeptides which include an amino acid sequence corresponding (e.g., identical or homologous) to all or a portion of the amino acid sequences of a GLC1A protein shown in SEQ ID No: 3 and which mimic or antagonize all or a portion of the biological/biochemical activities of a naturally occurring GLC1A protein. In preferred embodiments, the biochemical activities are related to gene expression, pituitary development, and abdominal development related to umbilical and vitelline artery expression.

Other biological activities of the subject GLC1A proteins are described herein or will be reasonably apparent to those skilled in the art. According to the present invention, a polypeptide has biological activity if it is a specific agonist or antagonist of a naturally-occurring form of a GLC1A protein.

The present invention further pertains to methods of producing the subject GLC1A polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant GLC1A polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant GLC1A polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject GLC1A polypeptides which function in a limited capacity as one of either a GLC1A agonist (mimetic) or a GLC1A antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of GLC1A proteins.

Homologs of each of the subject GLC1A proteins can be generated by mutagenesis, such as by discrete point mutation(s), or by truncation. For instance, mutation can give rise to homologs which retain substantially the same, or merely a subset, of the biological activity of the GLC1A polypeptide from which it was derived. Alternatively, antagonistic forms of the protein can be generated which are able to inhibit the function of the naturally occurring form of the protein, such as by competitively binding to a downstream or upstream member of the biochemical pathway, which includes the GLC1A protein. In addition, agonistic forms of the protein may be generated which are constitutively active. Thus, the human GLC1A protein and homologs thereof provided by the subject invention may be either positive or negative regulators of gene expression.

The recombinant GLC1A polypeptides of the present invention also include homologs of the authentic GLC1A proteins, such as versions of those protein which are resistant to proteolytic cleavage, as for example, due to mutations which alter ubiquitination or other enzymatic targeting associated with the protein.

GLC1A polypeptides may also be chemically modified to create GLC1A derivatives by forming covalent or aggregate conjugates with other chemical moieties, such as glycosyl groups, lipids, phosphate, acetyl groups and the like. Covalent derivatives of GLC1A proteins can be prepared by linking the chemical moieties to functional groups on amino acid sidechains of the protein or at the N-terminus or at the C-terminus of the polypeptide.

Modification of the structure of the subject GLC1A polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the GLC1A polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur - containing=cysteine and methionine. (see, for example, *Biochemistry,* 2nd ed., Ed. by L. Stryer, WH Freeman and Co.: 1981). Whether a change in the amino acid sequence of a peptide results in a functionalGLC1Ahomolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject GLC1A proteins as well as truncation mutants, and is especially useful for identifying potential variant sequences (e.g. homologs) that are functional in modulating gene expression. The purpose of screening such combinatorial libraries is to generate, for example, novel GLC1A homologs which can act as either agonists or antagonist, or alternatively, possess novel activities all together.

Likewise, GLC1A homologs can be generated by the present combinatorial approach to selectively inhibit gene expression. For instance, mutagenesis can provide GLC1A homologs which are able to bind other signal pathway proteins (or DNA) yet prevent propagation of the signal, e.g. the homologs can be dominant negative mutants. Moreover, manipulation of certain domains of GLC1A by the present method can provide domains more suitable for use in fusion proteins.

In one embodiment, the variegated library of GLC1A variants is generated by combinatorial mutagenesis at the nucleic acid level, and is encoded by a variegated gene library. For instance, a mixture of synthetic oligonucleotides can be enzymatically ligated into gene sequences such that the degenerate set of potential GLC1A sequences are expressible as individual polypeptides, or alternatively, as a set of larger fusion proteins (e.g. for phage display) containing the set of GLC1A sequences therein.

There are many ways by which such libraries of potential GLC1A homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential GLC1A sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier ppg. 273–289; Itakura et al. (1984) *Annu. Rev. Biochem.* 53:323; Itakura et al. (1984)

Science 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a GLC1A clone in order to generate a variegated population of GLC1A fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a GLC1A coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of GLC1A homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate GLC1A sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevier Publishing Co., Amsterdam, pp. 401–410; Delgrave et al., 1993, *Protein Engineering* 6(3):327–331).

The invention also provides for reduction of the GLC1A proteins to generate mimetics, e.g. peptide or non-peptide agents, which are able to disrupt binding of a mammalian GLC1A polypeptide of the present invention with either upstream or downstream components. Thus, such mutagenic techniques as described above are also useful to map the determinants of the GLC1A proteins which participate in protein-protein interactions involved in, for example, binding of the subject GLC1A polypeptide to proteins which may function upstream (including both activators and repressors of its activity) or to proteins or nucleic acids which may function downstream of the GLC1A polypeptide, whether they are positively or negatively regulated by it. To illustrate, the critical residues of a subject GLC1A polypeptide which are involved in molecular recognition of a component upstream or downstream of a GLC1A can be determined and used to generate GLC1A-derived peptidomimetics which competitively inhibit binding of the authentic GLC1A protein with that moiety. By employing, for example, scanning mutagenesis to map the amino acid residues of each of the subject GLC1A proteins which are involved in binding other extracellular proteins, peptidomimetic compounds can be generated which mimic those residues of the GLC1A protein which facilitate the interaction. Such mimetics may then be used to interfere with the normal function of a GLC1A protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), ketomethylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:123 1), and β-aminoalcohols (Gordon et al. (1985) *Biochem Biophys Res Commun* 126:419; and Dann et al. (1986) *Biochem Biophys Res Commun* 134:71).

4.4.1. Cells Expressing Recombinant GLC1A Polypeptides

This invention also pertains to a host cell transfected to express a recombinant form of the subject GLC1A polypeptides. The host cell may be any prokaryotic or eukaryotic cell. Thus, a nucleotide sequence derived from the cloning of GLC1A proteins, encoding all or a selected portion of the full-length protein, can be used to produce a recombinant form of a GLC1A polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, pg. 53, WT1, PTP phosphotases, SRC, and the like. Similar procedures, or modifications thereof, can be employed to prepare recombinant GLC1A polypeptides by microbial means or tissue-culture technology in accord with the subject invention.

The recombinant GLC1A genes can be produced by ligating nucleic acid encoding a GLC1A protein, or a portion thereof, into a vector suitable for expression in either prokaryotic cells, eukaryotic cells, or both. Expression vectors for production of recombinant forms of the subject GLC1A polypeptides include plasmids and other vectors. For instance, suitable vectors for the expression of a GLC1A polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP5 1, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a GLC1A polypeptide is produced recombinantly utilizing an expression vector generated by sub-cloning the coding sequence of one of the GLC1A genes represented in SEQ ID Nos: 1 and 2.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant GLC1A polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a GLC1A protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing GLC1A-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion Proteins and Immunogens

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a GLC1A protein. For example, the VP6 capsid protein of rotavirus can be used as an immunologic carrier protein for portions of the GLC1A polypeptide, either in the monomeric form or in the form of a viral particle. The nucleic acid sequences corresponding to the portion of a subject GLC1A protein to which antibodies are to be raised can be incorporated into a fusion gene construct which includes coding sequences for a late vaccinia virus structural protein to produce a set of recombinant viruses expressing fusion proteins comprising GLC1A epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a GLC1A protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a GLC1A polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of GLC1A proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the GLC1A polypeptides of the present invention. For example, GLC1A polypeptides can be generated as glutathione-S-transferase (GST-fusion) proteins. Such GST-fusion proteins can enable easy purification of the GLC1A polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al. John Wiley & Sons: 1992).

4.4.3. Antibodies

Another aspect of the invention pertains to an antibody specifically reactive with a GLC1A protein. For example, by using immunogens derived from a GLC1A protein, e.g. based on the cDNA sequences, anti-protein/anti-peptide antisera or monoclonal antibodies can be made by standard protocols (See, for example, Antibodies: *A Laboratory Manual* ed. by Harlow and Lane (Cold Spring Harbor Press: 1988)). A mammal, such as a mouse, a hamster or rabbit can be immunized with an immunogenic form of the peptide (e.g., a GLC1A polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a GLC1A protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a GLC1A protein of a mammal, e.g. antigenic determinants of a protein represented by SEQ ID No: 2 or closely related homologs (e.g. at least 92% homologous, and more preferably at least 94% homologous).

Following immunization of an animal with an antigenic preparation of a GLC1A polypeptide, anti-GLC1A antisera can be obtained and, if desired, polyclonal anti-GLC1A antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with a GLC1A polypeptide of the present invention and monoclonal antibodies isolated from a culture comprising such hybridoma cells.

The term antibody as used herein is intended to include fragments thereof which are also specifically reactive with one of the subject mammalian GLC1A polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a GLC1A protein conferred by at least one CDR region of the antibody.

Antibodies which specifically bind GLC1A epitopes can also be used in immunohistochemical staining of tissue samples in order to evaluate the abundance and pattern of expression of each of the subject GLC1A polypeptides. Anti-GLC1A antibodies can be used diagnostically in immuno-precipitation and immuno-blotting to detect and evaluate GLC1A protein levels in tissue as part of a clinical testing procedure. For instance, such measurements can be useful in predictive valuations of the onset or progression of proliferative disorders. Likewise, the ability to monitor GLC1A protein levels in an individual can allow determination of the efficacy of a given treatment regimen for an individual afflicted with such a disorder. The level of GLC1A polypeptides may be measured from cells in bodily fluid, such as in samples of cerebral spinal fluid or amniotic fluid, or can be measured in tissue, such as produced by biopsy. Diagnostic assays using anti-GLC1A antibodies can include, for example, immunoassays designed to aid in early diagnosis of a degenerative disorder, particularly ones which are manifest at birth. Diagnostic assays using anti-GLC1A polypeptide antibodies can also include immunoassays designed to aid in early diagnosis and phenotyping neoplastic or hyperplastic disorders.

Another application of anti-GLC1A antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a GLC1A protein, e.g. other orthologs of a particular GLC1A protein or other paralogs from the same species, can then be detected with antibodies, as, for example, reacting nitrocellulose filters lifted from infected plates with anti-GLC1A antibodies. Positive phage detected by this assay can then be isolated from the infected plate. Thus, the presence of GLC1A homologs can be detected and cloned from other animals, as can alternate isoforms (including splicing variants) from humans.

4.5 Methods of Treating Disease

There may be a variety of pathological conditions for which GLC1A therapeutics of the present invention can be used in treatment. Examples include glaucoma A "GLC1A therapeutic," whether an antagonist or agonist of wild type GLC1A, can be, as appropriate, any of the preparations described above, including isolated polypeptides, gene therapy constructs, antisense molecules, peptidomimetics, small molecules, non-nucleic acid, non-peptidic or agents identified in the drug assays provided herein.

Since, in some cases, genes may be upregulated in a disease state and in other cases may be downregulated, it will be desirable to activate and/or potentiate or suppress and/or downmodulate GLC1A bioactivity depending on the condition to be treated using the techniques compounds and methods described herein. Some genes may be underexpressed in certain disease states. The activity of GLC1A gene products may be in some way impaired, leading to the development of disease symptoms. Such down-regulation of GLC1A gene expression or decrease in the activity of a GLC1A protein may have a causative or exacerbating effect on the disease state.

Among the approaches which may be used to ameliorate disease symptoms involving the misexpression of a GLC1A gene are, for example, antisense, ribozyme, and triple helix molecules described above. Compounds that compete with a GLC1A protein for binding to upstream or downstream elements in a signaling cascade will antagonize a GLC1A protein, thereby inducing a therapeutic effect. Examples of suitable compounds include the antagonists or homologues described in detail above. In other instances, the increased expression or bioactivity of a GLC1A protein may be desirable and may be accomplished by, for example the use of the GLC1A agonists or mimetics or by gene replacement therapy, as described herein.

Compounds identified as increasing or decreasing GLC1A gene expression or protein activity can be administered to a subject at therapeutically effective dose to treat or ameliorate symptoms associated with glaucoma.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic GLC1A gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A GLC1A gene, such as any one of the sequences represented in the group consisting of SEQ ID NO: 1 or 3, or a sequence homologous thereto can be delivered in a gene therapy construct by electroporation using techniques described, for example, by Dev et al. ((1994) *Cancer Treat Rev* 20:105–115). Gene therapy vectors comprised of viruses that provide specific effective and highly localized treatment of eye diseases are described in Published International Patent Application No. WO 95/34580 to U. Eriksson et al.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic and Prognostic Assays

The following mutations have been identified in glaucoma patients: (1) GLN368STOP, (2) GLY364VAL, (3) TYR437HIS, (4) ILE477ASN, (5) a 6 bp insertion in codon 396, (6) VAL4951LE, (7) ALA445VAL, (8) THR377MET, (9) GLN19HIS, (10) ARG82CYS. In addition, the following polymorphisms have been identified in normal individuals: (1) TYR347TYR, (2) THR325THR, (3) VAL439VAL, (4) ARG398LYS and (5) Pro13Pro.

The prevalence of the sequence changes reported herein, coupled with the prevalence of glaucoma in the general population, suggests that mutations in the GLC1A gene cause glaucoma in nearly one hundred thousand patients in the United States. Therefore, the GLC1A gene is the most common molecularly recognizable form of blindness. For comparison, only two thousand people in the United States would be expected to harbor mutations in the rhodopsin gene, which is the most common form of molecularly recognizable retinitis pigmentosa. The discovery of specific glaucoma-causing mutations allows for identification of subjects at high risk for this form of glaucoma before significant visual loss has occurred, so that they can be directed toward sight-saving therapy.

In the diagnostic and prognostic assays described herein, in addition to the GLC1A nucleic acid molecules and polypeptides described above, the present invention provides for the use of nucleic acids comprising at least a portion of the nucleic acid sequence shown in SEQ ID Nos: 1 or 2 or polypeptides comprising at least a portion of the amino acid sequence shown in SEQ ID No: 3.

The present method provides a method for determining if a subject is at risk for glaucoma. In preferred embodiments, the methods can be characterized as comprising detecting, in a sample of cells from the subject, the presence or absence of a genetic lesion characterized by at least one of (i) an alteration affecting the integrity of a gene encoding a GLC1A-protein, or (ii) the mis-expression of the GLC1A gene. To illustrate, such genetic lesions can be detected by ascertaining the existence of at least one of (i) a deletion of one or more nucleotides from a GLC1A gene, (ii) an addition of one or more nucleotides to a GLC1A gene, (iii) a substitution of one or more nucleotides of a GLC1A gene, (iv) a gross chromosomal rearrangement of a GLC1A gene, (v) a gross alteration in the level of a messenger RNA transcript of a GLC1A gene, (vii) aberrant modification of a GLC1A gene, such as of the methylation pattern of the genomic DNA, (vii) the presence of a non-wild type splicing pattern of a messenger RNA transcript of a GLC1A gene, (viii) a non-wild type level of a GLC1A-protein, (ix) allelic loss of a GLC1A gene, and (x) inappropriate post-translational modification of a GLC1A-protein. As set out below, the present invention provides a large number of assay techniques for detecting lesions in a GLC1A gene, and importantly, provides the ability to discern between different molecular causes underlying GLC1A-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a GLC1A gene, such as represented by any of SEQ ID Nos: 1 and 2, or naturally occurring mutants thereof, or 5' or 3' flanking sequences or intronic sequences naturally associated with the subject GLC1A genes or naturally occurring mutants thereof The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more GLC1A of the sample cells. The present method provides a method for determining if a subject is at risk for a disorder characterized by aberrant cell proliferation and/or differentiation. In preferred embodiments, the method can be generally characterized as comprising detecting, in a sample of cells from the subject, the presence or absence of a genetic lesion characterized by an alteration affecting the integrity of a gene encoding a GLC1A. To illustrate, such genetic lesions can be detected by ascertaining the existence of at least one of (i) a deletion of one or more nucleotides from a GLC1A-gene, (ii) an addition of one or more nucleotides to a GLC1A-gene, (iii) a substitution of one or more nucleotides of a GLC1A-gene, and (iv) the presence of a non-wild type splicing pattern of a messenger RNA transcript of a GLC1A-gene. As set out below, the present invention provides a large number of assay techniques for detecting lesions in GLC1A genes, and importantly, provides the ability to discern between different molecular causes underlying GLC1A-dependent aberrant cell growth, proliferation and/or differentiation.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the GLC1A-gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a GLC1A gene under conditions such that hybridization and amplification of the GLC1A-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a GLC1A gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the GLC1A gene and detect mutations by comparing the sequence of the sample GLC1A with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labelled) RNA or DNA containing the wild-type GLC1A sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GLC1A cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a GLC1A sequence, e.g., a wild-type GLC1A sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in GLC1A genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control GLC1A nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) Hum. Mol. Genet. 2:1719–21; van der Luijt, et. al., (1994) Genomics 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Another embodiment of the invention provides for a nucleic acid composition comprising a (purified) oligonucleotide probe including a region of nucleotide sequence which is capable of hybridizing to a sense or antisense sequence of a GLC1A-gene, or naturally occurring mutants thereof, or 5' or 3' flanking sequences or intronic sequences naturally associated with the subject GLC1A-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, neoplastic or hyperplastic disorders (e.g. aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a GLC1A gene.

Any cell type or tissue, preferably monocytes, endothelial cells, or smooth muscle cells, in which the GLC1A is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO 91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant GLC1A proteins, which are discussed, above, may also be used in disease diagnostics and prognostics. Such diagnostic methods, may be used to detect abnormalities in the level of GLC1A protein expression, or abnormalities in the structure and/or tissue, cellular, or subcellular location of GLC1A protein. Structural differences may include, for example, differences in the size, electronegativity, or antigenicity of the mutant GLC1A protein relative to the normal GLC1A protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of GLC1A proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the GLC1A protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-GLC1A protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay,* CRC Press, Boca Raton, Fla., 1980; Ishikawa, et al., (eds.) *Enzyme Immunoassay,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a GLC1A gene or gene product can be used to monitor the course of treatment or therapy.

4.7. Drug Screening Assays

Based on the identification of specific GLC1A mutations in human beings with glaucoma, one of skill in the art can use any of a number of standard assays to screen for drugs, which will interfere with or otherwise prevent the development of glaucoma. By addressing the molecular basis of glaucoma, these agents are expected to be superior to existing therapies.

For example, identification of the precise phenotype associated with these mutations can be used to identify functionally important regions of the protein. These specific mutations can then be used in other experiments which will include overexpression in cell lines and the creation of transgenic animals. Ideally, one could identify mutations which reproducibly cause glaucoma at very different times in the person's life and then be able to show that these mutations had similar differences of effect in a cellular expression system or a transgenic animal.

Although GLC1A likely causes glaucoma through its actions within the trabucular meshwork or ciliary body, it will be important to characterize the expression of this gene throughout the eye and indeed throughout the body to make sure that an important part of the pathogenesis of GLC1A-linked glaucoma is not caused by an indirect mechanism. Therefor identifying tissue distribution and the developmental time course of gene expression (at both protein and DNA levels) using standard procedures will be important.

In addition, identification of proteins that interact with the GLC1A gene product and genes encoding the proteins can performed, since proteins that interact with GLC1A gene product will be important targets for involvement in the pathogenesis of various types of glaucoma.

Further, studies will be undertaken to discover whether mutations known to cause glaucoma in human beings alter protein trafficking in tissue culture as well as animal models, since one mechanism through which mutations in the GLC1A gene could cause disease would be to alter the expression of other important gene products. This can occur by affecting overall protein trafficking within the cell caused for example by increased removal of mutant proteins at the level of the endoplasmic reticulum.

In addition to the pathogenic studies described above, the precise location and sequence of the introns within the GLC1A gene can be identified so that improved PCR-based screening assays can be developed to fully assay the coding sequences of the GLC1A in patients with glaucoma. Also, sequences that participate in the regulation of the GLC1A gene will be important to characterize. For example, some glaucoma-causing mutations in the GLC1A gene exist in upstream sequences which alter the expression of the gene either positively or negatively. Further, classes of genes that are similarly regulated may be important in glaucoma (for example genes that share upstream regulatory sequences with the GLC1A gene).

Further understanding of the pathogenesis of glaucoma is useful for identifying new classes of drugs which can be useful in the treatment of glaucoma. For example, preliminary data suggest that the GLC1A gene is induced by exposure of cells to steroids. Therefore, drugs which are capable of blocking this steroid effect can be tested for the ability to prevent or delay the development of glaucoma.

As further described below, in vitro assays which are suitable for very high throughput screening of compounds can be performed. As the simplest example of this approach, one could use antibodies to the GLC1A gene product to develop a simple ELISA assay for the induction of the GLC1A gene product and then perform this assay in a 96 well microtiter plate format to screen a large number of drugs for the efficacy in blocking the steroid induction of the gene product. In this way, automated methods could be used to screen several thousand potentially therapeutic compounds for efficacy.

Also, knowledge of the structure/function of the GLC1A gene immediately suggests other genes which might be involved in glaucoma. Such clues will come from studies of homology, evolution, evaluation of structural motifs within the gene, and genetic studies using analyses designed to identify genes causing polygenic disease.

In the original linkage study described herein, it was recognized that 3 of 22 obligate carriers of the glaucoma gene failed to manifest a severe glaucoma phenotype. This information suggests that other genes are capable of mitigating the effect of the GLC1A mutation. One powerful way to search for such mitigator genes is to express a glaucoma-causing gene in different backgrounds. This can be done by creating transgenic animals and then breeding the glaucoma-causing gene on different genetic mouse strains. If the phenotype is altered in different strains these animals can be back crossed in such a way that the mitigating gene can be identified.

Some of the assays mentioned above, will now be described in further detail below.

4.7.1 Cell-free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the GLC1A polypeptide, whether they are positively or negatively regulated by it. To the mixture of the compound and the upstream or downstream element is then added a composition containing a GLC1A polypeptide. Detection and quantification of complexes of GLC1A with it's upstream or downstream elements provide a means for determining a compound's efficacy at inhibiting (or potentiating) complex formation between GLC1A and a GLC1A-binding element. The efficacy of the compound can be assessed by generating dose response curves from data obtained using various concentrations of the test compound. Moreover, a control assay can also be performed to provide a baseline for comparison. In the control assay, isolated and purified GLC1A polypeptide is added to a composition containing the GLC1A-binding element, and the formation of a complex is quantitated in the absence of the test compound.

Complex formation between the GLC1A polypeptide and a GLC1A binding element may be detected by a variety of techniques. Modulation of the formation of complexes can be quantitated using, for example, detectably labeled proteins such as radiolabeled, fluorescently labeled, or enzymatically labeled GLC1A polypeptides, by immunoassay, or by chromatographic detection.

Typically, it will be desirable to immobilize either GLC1A or its binding protein to facilitate separation of complexes from uncomplexed forms of one or both of the proteins, as well as to accommodate automation of the assay. Binding of GLC1A to an upstream or downstream element, in the presence and absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/GLC1A (GST/GLC1AA) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated.

Alternatively, the complexes can be dissociated from the matrix, separated by SDS-PAGE, and the level of GLC1A-binding protein found in the bead fraction quantitated from the gel using standard electrophoretic techniques such as described in the appended examples.

Other techniques for immobilizing proteins on matrices are also available for use in the subject assay. For instance, either GLC1A or its cognate binding protein can be immobilized utilizing conjugation of biotin and streptavidin. For instance, biotinylated GLC1A molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with GLC1A but which do not interfere with binding of upstream or downstream elements can be derivatized to the wells of the plate, and GLC1A trapped in the wells by antibody conjugation. As above, preparations of a GLC1A-binding protein and a test compound are incubated in the GLC1A-presenting wells of the plate, and the amount of complex trapped in the well can be quantitated. Exemplary methods for detecting such complexes, in addition to those described above for the GST-immobilized complexes, include immunodetection of complexes using antibodies reactive with the GLC1A binding element, or which are reactive with GLC1A protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the GLC1A-BP. To illustrate, the GLC1A-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-GLC1A antibodies, can be used. Alternatively, the protein to be detected in the complex can be "epitope tagged" in the form of a fusion protein which includes, in addition to the GLC1A sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

4.7.2. Cell Based Assays

In addition to cell-free assays, such as described above, the readily available source of mutant and functional GLC1A nucleic acids and proteins provided by the present invention also facilitates the generation of cell-based assays for identifying small molecule agonists/antagonists and the like. For example, cells can be caused to overexpress a recombinant GLC1A protein in the presence and absence of a test agent of interest, with the assay scoring for modulation in GLC1A responses by the target cell mediated by the test agent. As with the cell-free assays, agents which produce a statistically significant change in GLC1A-dependent responses (either inhibition or potentiation) can be identified. In an illustrative embodiment, the expression or activity of a GLC1A is modulated in cells and the effects of compounds of interest on the readout of interest (such as tissue differentiation, proliferation, tumorigenesis) are measured. For example, the expression of genes which are up- or down-regulated in response to a GLC1A-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cells or cell lines may be derived from ocular tissue (e.g. trabecular meshwork or ciliary body epithelia); as well as generic mammalian cell lines such as HeLa cells and COS cells, e.g., COS-7 (ATCC# CRL-1651). Further, the transgenic animals discussed herein may be used to generate one or more cell lines containing one or more cell types involved in glaucoma, that can be used as cell culture models for this disorder. While primary cultures derived from the glaucomatous transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Using these cells, the effect of a test compound on a variety of end points can be tested including cell proliferation, migration, phagocytosis, adherence and/or biosynthesis (e.g. of extracellular matrix components). The cells can then be examined for phenotypes associated with glaucoma, including, but not limited to changes in cellular morphology, cell proliferation, cell migration, and cell adhesion.

In the event that the GLC1A proteins themselves, or in complexes with other proteins, are capable of binding DNA and modifying transcription of a gene, a transcriptional based assay could be used, for example, in which a GLC1A responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject GLC1A polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with GLC1A ("GLC1A-binding proteins" or "GLC1A-bp.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a GLC1A polypeptide. The second hybrid protein encodes a transcriptional activation domain fused in frame to a sample gene from a cDNA library. If the bait and sample hybrid proteins are able to interact, e.g., form a GLC1A-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the GLC1A and sample proteins.

4.8 Transgenic Animals 4.8.1. Animal-based Systems

Another aspect of the present invention concerns transgenic animals which are comprised of cells (of that animal) which contain a transgene of the present invention and which preferably (though optionally) express an exogenous GLC1A protein in one or more cells in the animal. A GLC1A transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a GLC1A protein can be essential for many forms of lineage analysis and can additionally provide a means to assess the effects of, for example, lack of GLC1A expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject GLC1A proteins. For example, excision of a target sequence which interferes with the expression of a recombinant GLC1A gene, such as one which encodes an antagonistic homolog or an antisense transcript, can be designed to activate expression of that gene. This interference with expression of the protein can result from a variety of mechanisms, such as spatial separation of the GLC1A gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant GLC1A protein can be regulated via control of recombinase expression.

Use of the cre/loxP recombinase system to regulate expression of a recombinant GLC1A protein requires the construction of a transgenic animal containing transgenes encoding both the Cre recombinase and the subject protein. Animals containing both the Cre recombinase and a recombinant GLC1A gene can be provided through the construction of "double" transgenic animals. A convenient method for providing such animals is to mate two transgenic animals each containing a transgene, e.g., a GLC1A gene and recombinase gene.

One advantage derived from initially constructing transgenic animals containing a GLC1A transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic GLC1A transgene is silent will allow the study of progeny from that founder in which disruption of GLC1A mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the GLC1A transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a GLC1AA transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a GLC1A protein (either agonistic or antagonistic), and antisense transcript, or a GLC1A mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, Supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a GLC1A gene of interest in ES cells, these changes can be introduced into the germlines of animals to generate chimeras. The gene targeting procedure is accomplished by introducing into tissue culture cells a DNA targeting construct that includes a segment homologous to a target GLC1A locus, and which also includes an intended sequence modification to the GLC1A genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a GLC1A gene function through the use of a targeting transgene construct designed to undergo homologous recombination with one or more GLC1A genomic sequences. The targeting construct can be arranged so that, upon recombination with an element of a GLC1A gene, a positive selection marker is inserted into (or replaces) coding sequences of the gene. The inserted sequence functionally disrupts the GLC1A gene, while also providing a positive selection trait. Exemplary GLC1A targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. MoGLC1Ahol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no.

CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the GLC1A coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme (s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the GLC1A gene knocked out in various tissues of the offspring by probing the Western blot with an antibody against the particular GLC1A protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a GLC1A-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following examples which should not be construed as limiting in any way. The contents of all cited references (including literature references, issued patents, published patent applications, and co-pending patent applications) cited throughout this application are hereby expressly incorporated by reference.

5. 1 Genetic Linkage of Familial Open Angle Glaucoma to Chromosome 1q21-q31

Materials and Methods

Pedigree

A family in which five consecutive generations have been affected with juvenile-onset, open-angle glaucoma without iridocorneal angle abnormalities was identified. The family comprised descendants of a woman who emigrated from Germany to the midwestern United States in the late 1800s. The disease state in affected family members included onset during the first 3 decades of life, normal anterior chamber angles, high intraocular pressures, lack of systemic or other ocular abnormalities, and need for surgery to control the glaucoma in affected individuals. A total of 35 family members at 50% risk for glaucoma had complete eye examinations including visual acuity with refraction, slit-lamp biomicroscopy, applanation tomometry, gonioscopy, stereo disc photography and Humphrey, Goldmann or Octopus perimetry. Two other affected patients were ascertained by reviewing records of other ophthalmologists. Patients were considered to be affected for linkage if they had documented pressures greater than 30 mm Hg and evidence of optic nerve or visual field damage; or, if they had intraocular pressures greater than 22 mm Hg and an obviously affected child. Affected family members are characterized by an early age of diagnosis, a normal appearing trabecular meshwork, very high intraocular pressures (often above 50 mm Hg), and relatively pressure-resistant optic nerves. FIG. 1 is a pictorial representation of the pedigree.

DNA Typing

Blood samples were obtained from all living affected family members as well as six spouses of affected patients with children. 10 ml blood were obtained from each patient in EDTA-containing glass tubes. DNA was prepared from the blood using a non-organic extraction procedure (Grimberg, J. et al. Nucl. Acids Res 17, 8390 (1989)). Short tandem repeat polymorphisms (STRPs) distributed across the entire autosomal genome were selected from the literature or from those kindly provided by J. L. Weber. The majority were [dC-dA]-[dG-dT] dinucleotide repeats. Oligonucleotide primers flanking each STRP were synthesized using standard phosphoramidite chemistry (Applied Biosystems model 391 DNA synthesizer). Amplification of each STRP was performed with 50 ng. of each patient's DNA in a 8.35 l PCR containing each of the following: 1.25 l 10×buffer (100 mM Tris-HCl pH 8.8, 500 mM KCl, 15 mM $MgCl_2$, 0.01% w/v gelatin), 300 M each of dCTP, dGTP and dTTP, 37M dATP, 50 pmoles each primer, 0.25 l-$^{35}$S-dATP (Amersham,>1000 Ci mmol-$^{-1}$), and 0.25 U Taq polymerase (Perkin-Elmer/Cetus). Samples were incubated in a DNA thermocycler (Perkin-Elmer/Cetus) for 35 cycles under the following conditions: 94 C. for 30 s, 55 C. for 30 s, and 72 C. for 30 s. Following amplification, 51 of stop solution (95% formamide, 10 mM NaOH, 0.05% Bromophenol Blue, 0.05% Xylene Cyanol) was added to each sample. Following denaturation for 3 min at 95 C., 5 l of each sample was immediately loaded onto prewarmed polyacrylamide gels (6% polyacrylamide, 7 M urea) and electrophoresed for 3–4 h. Gels were then placed on Whatman, 3mm paper and dried in a slab gel dryer. Autoradiographs were created by exposing Kodak Xomat AR film to the dried gels for 24–36 h.

Linkage Analysis

Genotypic data from the autoradiographs were entered into a Macintosh computer. A Hypercard-based program (Nichols, B E et al., Am J Hum Genet 51 A369 (1992)) was used to store and retrieve marker data as well as to export it to a DOS-compatible machine for analysis with the computer program LINKAGE (version 5.1) (Lathrop, G M and LaLouel, J M 359, 794–801 (1992)). Allele frequencies were assumed to be equal for each marker. The MLINK routine was used for pairwise analysis. The relative odds of all possible orders of the disease and two markers (D1S191 and D1S194) was performed under the ILINK program. Significance of linkage was evaluated using the standard criterion ($Z_{max}$>3.0).

Results

Clinical Findings

All of the 37 family members studied were at 50% risk of having the disease because of a known affected parent or sibling. Nineteen of these patients had elevated intraocular pressures and visual field defects consistent with the diagnosis of primary open angle glaucoma. Three more patients had moderately elevated intraocular pressures and obviously affected children.

Linkage Analysis

Over 90 short tandem repeat polymorphisms were typed in the family before linkage was detected with markers that map to the long arm of chromosome 1. Two-point maximum likelihood calculations using all available family members and 33 chromosome 1 markers revealed significant linkage to eight of them (Table 2). D1S212 was fully informative for all affected members of the family, and pairwise linkage analysis produced a lod score of 6.5 (=0). Multipoint linkage analysis did not add to the peak lod score. The glaucoma locus was therefore determined to be located in a region of about 20 centiMorgans (cM) in size between D1S191 and D1S194. Both of these markers demonstrated multiple recombinants (two and three, respectively) in affected individuals in the family. The order D1S191-glaucoma-D1S194 was more than 1,000 times more likely than the other two possible orders.

glaucoma locus. Using STRPs, the genotype of each family member was determined. Amplification of each STRP was performed using the following protocol:
1) Dilute genomic DNA (about 1 g/l) 1/50 i.e. 201 "stock" DNA and 980 dd $H_2O$.
2) Use 2.51 of "dilute" DNA as template for PCR
3) Prepare PCR reaction mix as follows:
   1.25 1 10×Buffer (Stratagene)
   0.12 1 of each primer (50 pmoles each primer)
   0.5 1 dNTPs (5mM C,T,&G and 0.625 mM A "cold")
   3.5 1 dd $H_2O$
   0.25 1 $^{35}$S-dATP
   0.1 1 Taq polymerase
   oil (one drop)
4) Perform PCR at optimal conditions for given primers (usually 94 30 s, 55 30s and 72 30 s) and run for 35 cycles.
5) Add 5 1 stop solution (95% formamide, 10 mM NaOH, 0.05% bromophenol blue, 0.05% xylene cyanol) to each tube.
6) Denature samples at 95 C. for 3 minutes and load immediately onto a prewarmed polyacrylamide gel.
7) Dry gels on Whatmann paper and expose autoradiography film for 1–2 days.

Where possible, multiple loadings of different STRPs on gels were performed. Up to 6 markers per gel have been successfully loaded. In addition, the PCR amplification (up to three markers) have been successfully multiplexed. The juvenile glaucoma gene is believed to lie between markers AFM238 and AT3 (an 8 centimorgan interval) based on observed recombinations within the families studied. Haplotypic analysis between families has further narrowed this interval to the 2 centimorgan interval between D1S210 and AT3.

TABLE 3

Pairwise linkage data
Recombination Fraction

|        | 0.15 | 0.20 | 0.25 | 0.30 | 0.40 | $Z_{max}$ |      |      | Locus   |
|--------|------|------|------|------|------|-----------|------|------|---------|
| D1S212 | 6.0  | 5.4  | 4.8  | 4.2  | 3.6  | 2.9       | 1.4  | 6.5  | 0.00    | 1 |
| D1S215 | 5.1  | 4.6  | 4.0  | 3.5  | 2.9  | 2.3       | 1.0  | 5.6  | 0.00    | 1 |
| D1S218 | 4.7  | 4.3  | 3.8  | 3.3  | 2.7  | 2.2       | 1.0  | 5.2  | 0.00    | 1 |
| D1S238 | 4.4  | 4.2  | 3.9  | 3.4  | 2.9  | 2.4       | 1.2  | 4.4  | 0.04    | 1 |
| D1S117 | 3.8  | 3.6  | 3.3  | 2.8  | 2.3  | 1.8       | 0.7  | 3.8  | 0.04    | 1q |
| D1S104 | 3.2  | 2.9  | 2.6  | 2.3  | 2.0  | 1.6       | 0.7  | 3.4  | 0.00    | 1q21-q23 |
| D1S191 | 3.0  | 3.2  | 3.0  | 2.7  | 2.4  | 1.9       | 0.9  | 3.2  | 0.09    | 1 |
| D1S196 | 2.9  | 2.6  | 2.3  | 2.0  | 1.6  | 1.3       | 0.5  | 3.1  | 0.00    | 1 |

Table 2 Pairwise Linkage Data Recombination Fraction
0.05
0.19

5.2 Genetic Fine Mapping of the Juvenile Primary Open Angle Glaucoma Locus and Identification and Characterization of a Glaucoma Gene Once primary linkage has been identified, the next step in identifying any disease gene by positional cloning is the narrowing of the candidate locus to the smallest possible genetic region. The initial study described in Example 5.1 demonstrated that a primary open angle glaucoma gene lies within an approximately 20 cM region flanked by markers D1S194 and D1S191 on chromosome 1q. Additional markers and families were obtained and used to refine the genetic locus to a 2.5 cM region using two of these families. The third family should allow the interval to be further narrowed.

In addition to the family resources, polymorphic DNA markers and genetic maps were used to refine the 1q glaucoma locus. Using STRPs, the genotype of each family Since the genetic interval has been narrowed significantly physical mapping strategies can be used. The closest flanking markers to screen total human genomic yeast artificial chromosome (YAC) libraries to identify YACs mapping to the region of interest. The CEPH and CEPH mega-YAC libraries can be used for this purpose (available from the Centre d'Etude du Polymorphisme Humain (CEPH) Paris, France). Forty-four percent of the clones in the CEPH mega-YAC library have an average size of 560 kb, an additional 21% have an average size of 800 kb, and 35% have an average size of 120 kb. This library is available in a gridded micro-titer plate format such that only 50–200 PCR reactions need to be performed using a specific sequence tagged site (STS) to identify a unique YAC containing the STS. The YAC contigs identified by CEPH have been used to begin constructing a contig across the 1q candidate region (see FIG. 3). YAC contigs using YAC ends can be constructed to identify additional YACs. YAC ends can be rescued using anchored PCR (Riley, J. et al (1990) *Nucleic Acids Res* 18:2887–2890), the ends can then be sequenced and the sequence can be used to develop a sequence tagged site (STS). The STS can be used to rescreen the YAC library to obtain an overlapping adjacent YAC.

Because some YACs have been shown to be chimeric or to contain deletions or rearrangements, particularly those from the mega YAC library, the correctness of each YAC contig should be verified by constructing a pulse field map of the region. In addition, chimeric YACs are minimized by ensuring that the YAC maps to a single chromosome by fluorescent in situ hybridization (FISH) or that the two YAC ends map to the same chromosome using monochromosomal somatic cell hybrids (NIGMs Panel 2). In addition, the YAC chimera problem can be minimized by not relying on any single YAC to span a given chromosome segment, but rather by obtaining at least two overlapping independent YACs to ensure coverage of a given region.

Once a YAC contig spanning the candidate region has been isolated, this reagent can be used to generate additional genetic markers for potentially finer genetic mapping. In addition, the YACs can be used to make higher resolution physical mapping reagents such as region specific lambda and cosmid clones. Lambda and cosmid clones can be used for isolation of candidate genes. A modification of "exon trapping" (Duyk, G. M. (1990) *Proc Natl Acad Sci USA* 87:8995–8999) known as exon amplification (Buckler, A. J. (1991) *Proc Natl Acad Sci USA* 88:4005–4009) can be used to identify exons from genes within the region. Exons trapped from the candidate region can be used as probes to screen eye cDNA libraries to isolate cDNAs. Where necessary, other strategies can be utilized to identify genes in genomic DNA including screening cDNA libraries with YAC fragments subcloned into cosmids, zoo blot analysis, coincidence cloning strategies such as direct selection of cDNAs with biotin-streptavidin tagged cosmid clones (Morgan, J. G. et al (1992) *Nucleic Acid Res* 20 (19) :5173–5179), and HTF island analysis (Bird, A. P. (1987) *Trends Genet* 3:342–247). Promising genes will be further evaluated by searching for mutations using GC-clamped denaturing gradient gel electrophoresis (Sheffield, V. C. et al (1989) *Genomics* 16:325–332), single strand conformational gel polymorphism (SSCP) analysis (Orita, M. et al (1989) *Proc Natl Acad Sci USA* 86:2766–2770) and direct DNA sequencing.

5.3 Primer Pairs for Use In Identifying Subjects Having a Predisposition to Glaucoma Two primer pairs that can be used in conjunction with the polymerase chain reaction to amplify a 190 base pair sequence from human genomic DNA that harbors mutations causing glaucoma (primers 1 and 2 in Table 3) have been identified.

TABLE 3

| Primer 1 | |
|---|---|
| forward - ATACTGCCTAGGCCACTGGA | (SEQ ID NO.4) |
| reverse - CAATGTCCGTGTAGCCACC | (SEQ ID NO.5) |
| Primer 2 | |
| forward - GAACTCGAACAAACCTGGGA | (SEQ ID NO.6) |
| reverse - CATGCTGCTGTACTTATAGCGG | (SEQ ID NO.7) |

These primers which hybridize to a portion of the Trabecular Meshwork Induced Glucocorticoid (TIGR) gene (International Publication No. 96/14411 to Nguyen et al.) were used to screen 410 patients with glaucoma and 81 normal individuals. Four amino acid altering sequence changes were detected in a total of 12 glaucoma patients (2.9%). No amino acid altering sequence changes were observed in the normal individuals.

The specific mutations observed are shown in FIG. 4 below the normal sequence. The prevalence of mutations in the segment of DNA amplified by these primer pairs suggest that use of these primers in conjunction with an appropriate detection method can be used to identify a predisposition to glaucoma in approximately 100 thousand patients in the United States alone.

What is claimed is:

1. An isolated nucleic acid molecule comprising a nucleic acid molecule as set forth in SEQ ID No: 1 or the complement thereof.

2. An isolated nucleic acid molecule of claim 1, which further comprises a detectable label.

3. A vector comprising the nucleic acid molecule of claim 1.

4. A vector of claim 3, which can replicate in a cell.

5. An isolated host cell comprising a vector of claim 3.

6. An isolated nucleic acid molecule comprising SEQ ID No: 1, which encodes a GLC1A polypeptide.

* * * * *